US006359054B1

(12) United States Patent
Lemieux et al.

(10) Patent No.: US 6,359,054 B1
(45) Date of Patent: *Mar. 19, 2002

(54) POLYNUCLEOTIDE COMPOSITIONS FOR INTRAMUSCULAR ADMINISTRATION

(75) Inventors: Pierre M. Lemieux, Ste.-Therese (CA); Alexander V. Kabanov, Omaha, NE (US); Valery Y. Alakov, D'Urfe (CA); Sergey V. Vinogradov, Omaha, NE (US)

(73) Assignee: Supratek Pharma Inc., Doryal ( * ) Notice: Subject to any disclaimer, the term of this patent is extended or adjusted under 35 U.S.C. 154(b) by 0 days.

This patent is subject to a terminal disclaimer.

(21) Appl. No.: 09/227,364

(22) Filed: Jan. 8, 1999

Related U.S. Application Data

(63) Continuation-in-part of application No. 09/124,943, filed on Jul. 30, 1998, now Pat. No. 6,221,959, which is a continuation-in-part of application No. 08/912,968, filed on Aug. 1, 1997, which is a continuation-in-part of application No. 08/342,209, filed on Nov. 18, 1994, now Pat. No. 5,656,611.

(51) Int. Cl.$^7$ ............................ C08L 53/00; C07H 21/00

(52) U.S. Cl. ...................... 524/505; 524/612; 525/92 A; 525/92 L; 424/426; 536/23.7; 536/24.1; 536/24.31; 536/24.5

(58) Field of Search ................................ 524/612, 505; 525/54.2, 92 A, 92 L; 424/426; 536/23.7, 24.1, 24.31, 24.5

(56) References Cited

U.S. PATENT DOCUMENTS

| | | | |
|---|---|---|---|
| 4,801,452 A | 1/1989 | Hunter et al. | 424/94.63 |
| 4,873,083 A | 10/1989 | Hunter et al. | 424/83 |
| 4,879,109 A | 11/1989 | Hunter | 424/83 |
| 5,017,370 A | 5/1991 | Hunter et al. | 424/83 |
| 5,030,448 A | 7/1991 | Hunter | 424/83 |
| 5,041,288 A | 8/1991 | Hunter | 424/83 |
| 5,047,236 A | 9/1991 | Hunter et al. | 424/83 |
| 5,470,568 A | 11/1995 | Lee | |
| 5,531,925 A | 7/1996 | Landh et al. | 428/1 |
| 5,547,932 A | 8/1996 | Curiel et al. | |
| 5,552,309 A | 9/1996 | March | |
| 5,569,468 A | 10/1996 | Modi | |
| 5,573,934 A | * 11/1996 | Hubbell et al. | |
| 5,589,466 A | 12/1996 | Felgner et al. | |
| 5,605,687 A | 2/1997 | Lee | |
| 5,656,611 A | 8/1997 | Kabanov et al. | 514/44 |
| 5,679,647 A | 10/1997 | Carson et al. | |
| 5,693,622 A | 12/1997 | Wolff et al. | |
| 5,698,529 A | 12/1997 | Alakhov et al. | 514/34 |
| 5,770,580 A | 6/1998 | Ledley et al. | |
| 5,797,870 A | 8/1998 | March et al. | |
| 5,840,319 A | 11/1998 | Alakhov et al. | 424/400 |
| 6,040,295 A | 3/2000 | Rolland et al. | 514/44 |

OTHER PUBLICATIONS

Feldman et al.; Improved Efficiency of Arterial Gene Transfer by Use of Poloxamer 407 as a Vehicle for Adenoviral Vectors; Gene Therapy; 4:3; Mar. 1997; 189–198.
Van Belle et al.; Effect of Poloxamer 407 on Transfection Time and Percutaneous Adenovirus–Mediated Gene Transfer in Native and Stented Vessels; Human Gene Therapy; 9:7; May 1998; 1013–1024.
March et al.; Pharmacokinetics of Adenoviral Vector–Mediated Gene Delivery to Vascular Smooth Muscle Cells: Modulation by Poloxamer 407 and Implications for Cardiovascular Gene Therapy; Human Gene Therapy; 6:1; Jan., 1995; 41–53.
Mortensen and Pedersen, *Macromolecules* (1993), 26:805–812.
Linse, *Macromolecules* (1993), 26:4437–4449.
Mortensen and Brown, *Macromolecules* (1993), 26:4128–4135.
Schillen et al., *Macromolecules* (1994), 27:4825–4832.
Schillen et al., *Macromolecules* (1993), 26:3611–3614.
Linse, *Macromolecules* (1994), 27:2685–2693.
Zhou and Chu, *Macromolecules* (1994), 27:2025–2033.
Zhou and Chu, *Journal of Colloid and Interface Science* (1988), 126:171–180.
Zhou and Chu, *Macromolecules* (1988), 21:2548–2554.
Alexandridis, *Macromolecules* (1994), 27:2414–2425.
Alexandridis, *Langmuir* (1994), 10:2604–2612.
Hecht and Hoffman, *Langmuir* (1994), 10:86–91.
Schmolka, *Journal of the Am. Oil Chemists' Society* (1977), 54:110–116.
Wilhelm et al., *Macromolecules* (1991), 24:1033–1040.
Hoes et al., *J. Controlled Release* (1995), 2:205–213.
Duncan et al., *J. Controlled Release* (1989), 10:51–63.
Pratesi et al., *Br. J. Cancer* (1985), 52:841–848.
Page and Alakhov, *Proc Ann Meet Am. Assoc Cancer Res* (1992), 33:A3302.
Summary of article in *Nikkei Weekly*, Feb. 1994.
Slepnev et al., *Biochemistry International*, (1992) 26:587–595.
Kabanov et al., *Biochemistry International*, (May, 1992) 26:1035–1042.
Kabanov et al., *FEBS Letters*, (Dec. 1989) 258:343–345.
Kabanov et al., *J. Controlled Release*, (1992) 22:141–158.
Chekhonin et al., *FEBS*, (1991) 287:149–152.
"Highlights of U.S. Patents," *Anti–Viral Agents Bulletin*, Dec. 1993.

(List continued on next page.)

Primary Examiner—Peter Szekely
(74) Attorney, Agent, or Firm—Mathews, Collins, Shepherd & Gould, P.A.

(57) ABSTRACT

Compositions and methods for intramuscular administration of polynucleotides, such as RNA, DNA, or derivatives thereof comprising polynucleotides and block copolymers of alkylethers. The invention also provides compositions and methods for stabilizing polynucleic acids and increasing the ability of polynucleic acids to cross cell membranes and act in the interior of a cell.

25 Claims, No Drawings

OTHER PUBLICATIONS

Kabanov et al., *Sov. Sci. Rev. D. Physiochem. Biol.* (1992), 11:1–75.

Kabanov et al., "Increasing the Transforming Activity of Plasmid DNA...," Plenum Publishing Corporation (1989), pp. 133–136.

Levashov et al., "Chemical Modification of Proteins (Enzymes) with Water Insoluble Reagents" (1984), pp. 295–297.

Levashov et al., "Translocation of Waterproofed Proteins (Enzymes) into Lysosymes" (1985).

Kabanov et al, *Collect. Czech. Chem. Commun.* (1989), 54:835–837.

Kabanov et al.; *FEBS Letters* (1989), 250:238–240.

Kabanov et al., *Biol. Memb.* (1989), 2:1769–1785.

Kabanov et al., *Protein Engineering* (1989), 3:39–42.

Martinek et al., *Biochemica et Biophysica Acta* (1989), 981:161–172.

Kabanov et al., *Biomedical Science* (1990), 1:33–36.

Alakhov et al., *Biotechnology & Applied Biochemistry* (1990), 12:94–98.

Severin et al., *Advances in Enzyme Regulation* (1990), pp. 417–430.

Kabanov et al., *Biomedical Science* (1990), 1:63–68.

Melik–Nubarov et al., "Immunotherapeutic Prospects of Infectious Diseases," Masihi and Lange., Eds., Springer–Verleg, Berlin (1990), pp. 385–388.

Kabanov et al., *Collect. Czech. Chem. Commun.* (1990), 55:587–589.

Kabanov et al., International Symposium on Virology, Immunology and Society, Kozminov and Radavsky, Eds., UNESCO, Venice (1991), pp. 303–322.

Slepnev et al., *Bioconjugate Chem.* (1992), 3:273–274.

Kabanov, International Conference on Pharmaceutical Ingredients and Intermediates, Published by Manufacturing Chemists (1992), pp. 89–96.

Melik–Nubarov et al., *Biochem. Molec. Biol. Int'l.* (1993), 29:939–947.

Kabanov et al., *Bioconjugate Chemistry* (1993), 4:448–454.

Sukhishvili et al., *Polymer Science* (1993), 35:1602–1606.

Kabanov and Alakhov, Sixth International Symposium on Recent Advances in Drug Delivery Systems (1993), pp. 73–76.

Kabanov and Alakhov, *J. Controlled Release* (1994), 28:15–35.

Kabanov et al., *FEBS Letters* (1990), 259:327–330.

Kabanov et al., *Bipolymers* (1994), 34:1437–1443.

Kabanov et al., *Polymer Preprints* (1991), 32:592–593.

Jones et al., *Bioconjugate Chem.* (1994), 5:390–399.

Wei, et al., *Bioconjugate Chem.* (1994), 5:464–478.

Jäsche et al., *Nucleic Acids Research* (1994), 22:4810–4817.

\* cited by examiner

POLYNUCLEOTIDE COMPOSITIONS FOR INTRAMUSCULAR ADMINISTRATION

This is a continuation-in-part of U.S. Ser. No. 09/124,943, filed Jul. 30, 1998, now U.S. Pat. No. 6,221,959, which is continuation-in-part of U.S. Ser. No. 08/912,968, filed Aug. 1, 1997, which in turn is a continuation-in-part of U.S. Ser. No. 08/342,209, filed Nov. 18, 1994, now U.S. Pat. No. 5,656,611.

FIELD OF THE INVENTION

The invention relates to block copolymer compositions and methods for intramuscular administration of polynucleotides.

BACKGROUND OF THE INVENTION

The unique features of smooth, skeletal, and cardiac muscles, have presented numerous challenges for the development and administration of effective polynucleotide compositions for intramuscular administration. Direct injection of purified plasmids ("naked DNA") in isotonic saline into muscle was found to result in DNA uptake and gene expression in smooth, skeletal, and cardiac muscles of various species. Rolland A., *Critical Reviews in Therapeutic Drug Carrier Systems*, Begell House, 143 (1998). It is believed that the unique cytoarchitectural features of muscle tissue are responsible for the uptake of polynucleotides because skeletal and cardiac muscle cells appear to be better suited to take-up and express injected foreign DNA vectors relative to other types of tissues. Dowty & Wolff, *Gene Therapeutics: Methods and Applications of Direct Gene Transfer*, Birkhäuser, Boston, p.182 (1994). The relatively low expression levels attained by this method, however, have limited its applications. See Aihara and Miyazaki, *Nature Biotechnology*, 16:867 (1998). Additionally, traditional gene delivery systems such as polycations, cationic liposomes, and lipids that are commonly proposed to boost gene expression in other tissues usually result in inhibition of gene expression in skeletal and cardiac muscles. Dowty & Wolff, *Gene Therapeutics: Methods and Applications of Direct Gene Transfer*, Birkhäuser, Boston, p. 82 (1994).

Anionic polymers such as dextran sulfate and salmon DNA can decrease gene expression in the muscle. Rolland A., *Critical Reviews in Therapeutic Drug Carrier Systems*, Begell House, 1998, p. 143. Various noncondensive interactive polymers have been used with a limited success to modify gene expression in striated muscle. Nonionic polymers such as poly(vinyl pyrrolidone) poly(vinyl alcohol) interact with plasmids through hydrogen bonding. Rolland A., *Critical Reviews in Therapeutic Drug Carrier Systems*, Begell House, 1998, p. 143. These polymers may facilitate the uptake of polynucleotides in muscle cells and cause up to 10-fold enhancement of gene expression. However, to achieve a significant increase in gene expression, high concentrations of polymers (about 5% and more) need to be administered. Mumper et al., *Pharmacol. Res.*, 13, 701–709 (1996); March et al., *Human Gene Therapy*, 6(1), 41–53 (1995). This high concentration of poly(vinyl pyrrolidone) poly(vinyl alcohol) needed to improve gene expression can be associated with toxicity, inflammation, and other adverse effects in muscle tissues. Block copolymers have been used to improve gene expression in muscle or to modify the physiology of the muscle for subsequent therapeutic applications. See U.S. Pat. Nos. 5,552,309; 5,470,568; 5,605,687; and 5,824,322. For example, block copolymers can be used in a gel-like form (more than 1% of block copolymers) to formulate virus particles used to perform gene transfer in the vasculature. In the same range of block copolymers concentration (1–10%), it is possible with block copolymer to modify the permeability of damaged muscle tissue (radiation and electrical injury, and frost bite). In addition DNA molecules can be incorporated into cells following membrane permeabilization with block copolymers. For these applications, block copolymers were used at concentrations giving gel-like structures and viscous delivery systems. These systems are unlikely to enable diffusion of the DNA injected into the muscle, however, thus limiting infusion of the DNA into the myofibers.

There is thus a need for compositions and methods increasing efficacy of polynucleotides expression upon administration in the muscle.

Beside the need to improve gene expression in muscle other tissues in the body would benefit from a gene transfer in a situation when there is a genetic disorder, and/or an abnormal over-expression of a gene, and/or absence of a normal gene. Several polynucleotides such as RNA, DNA, viruses, ribozymes can be used for gene therapy purposes. However, many problems, like the ones described below, have been encountered for successful gene therapies.

The use of antisense polynucleotides to treat genetic diseases, cell mutations (including cancer causing or enhancing mutations) and viral infections has gained widespread attention. This treatment tool is believed to operate, in one aspect, by binding to "sense" strands of mRNA encoding a protein believed to be involved in causing the disease site sought to be treated, thereby stopping or inhibiting the translation of the mRNA into the unwanted protein. In another aspect, genomic DNA is targeted for binding by the antisense polynucleotide (forming a triple helix), for instance, to inhibit transcription. See Helene, *Anti-Cancer Drug Design*, 6:569 (1991). Once the sequence of the mRNA sought to be bound is known, an antisense molecule can be designed that binds the sense strand by the Watson-Crick base-pairing rules, forming a duplex structure analogous to the DNA double helix. *Gene Regulation: Biology of Antisense RNA and DNA*, Erikson and lxzant, eds., Raven Press, New York, 1991; Helene, *Anti-Cancer Drug Design*, 6:569 (1991); Crooke, *Anti-Cancer Drug Design*, 6:609 (1991). A serious barrier to fully exploiting this technology is the problem of efficiently introducing into cells a sufficient number of antisense molecules to effectively interfere with the translation of the targeted mRNA or the function of DNA.

SUMMARY OF THE INVENTION

The invention relates to compositions of polynucleotides, such as RNA, DNA or their derivatives, and block copolymers. These compositions are useful for gene therapy purposes, including gene replacement or excision therapy, and gene addition therapy, vaccination, as well as therapeutic situations in which it is desirable to express or down-regulat a polypeptide in the body or in vitro.

DETAILED DESCRIPTION OF THE INVENTION

| DEFI-NITIONS | |
|---|---|
| As used herein, the terms below have the following meaning: | |
| Backbone: | Used in graft copolymer nomenclature to describe the chain onto which the graft is formed. |
| Block copolymer: | A combination of two or more chains of constitutionally or configurationally different features. |
| Branched polymer: | A combination of two or more chains linked to each other, in which the end of at least one chain is bonded at some point along the other chain. |
| Chain: | A polymer molecule formed by covalent linking of monomeric units. |
| Con-figuration: | Organization of atoms along the polymer chain, which can be interconverted only by the breakage and reformation of primary chemical bonds. |
| Con-formation: | Arrangements of atoms and substituents of the polymer chain brought about by rotations about single bonds. |
| Copolymer: | A polymer that is derived from more than one species of monomer. |
| Cross-link: | A structure bonding two or more polymer chains together. |
| Dendrimer: | A regularly branched polymer in which branches start from one or more centers. |
| Dispersion: | Particulate matter distributed throughout a continuous medium. |
| Graft copolymer: | A combination of two or more chains of con-stitutionally or configurationally different features, one of which serves as a backbone main chain, and at least one of which is bonded at some points along the backbone and constitutes a side chain. |
| Homo-polymer: | Polymer that is derived from one species of monomer. |
| Link: | A covalent chemical bond between two atoms, including bond between two monomeric units, or between two polymer chains. |
| Polymer blend: | An intimate combination of two or more polymer chains of constitutionally or configurationally different features, which are not bonded to each other. |
| Polymer fragment (or Polymer segment): | A portion of polymer molecule in which the monomeric units have at least one constitutional or configurational feature absent from adjacent portions. |
| Poly-nucleotide: | A natural or synthetic nucleic acid sequence. |
| Repeating unit: | Monomeric unit linked into a polymer chain. |
| Side chain: | The grafted chain in a graft copolymer. |
| Starblock copolymer: | Three or more chains of different constitutional or configurational features linked together at one end through a central moiety. |
| Star polymer: | Three or more chains linked together at one end through a central moiety. |
| Surfactant: | Surface active agent that is adsorbed at interface. |
| Viral vector: | A construct derived from a virus and used in gene transfer. |

Preferred embodiments include compositions having polynucleotides and block copolymers with cationic segments as well as compositions having polynucleotides and nonionic polyether block copolymers. In one embodiment, particularly useful for intramuscular administration, polynucleotides are formulated with block copolymers of poly(oxyethylene) and poly(oxypropylene).

The compositions of the current invention provide an efficient vehicle for introducing polynucleotides into a cell, protecting polynucleotides against degradation in body fluids, transport of polynucleotides across biological membranes and biological barriers (such as the blood-brain barrier, blood-cerebral fluid barrier, and intestinal barrier), modification of biodistribution of polynucleotides in the body and enhancement of gene expression including selective gene expression in various tissues and organs in the body of human or animal.

The invention further relates to methods of inserting polynucleotides into cells utilizing the compositions of the invention, and methods of treatment having administering these compositions in humans and animals.

In a preferred embodiment, the block copolymer conforms to one of the following formulae:

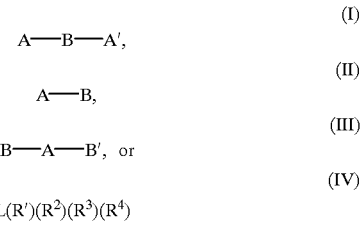

wherein A and A' are A-type linear polymeric segments, B and B' are B-type linear polymeric segments, and $R^1$, $R^2$, $R^3$, and $R^4$ are either block copolymers of formulas (I), (II), or (III), or hydrogen and L is a linking group, with the proviso that no more than two of $R^1$, $R^2$, $R^3$, or $R^4$ are hydrogen.

In another preferred embodiment, the block copolymers are poly(oxyethylene) and poly(oxypropylene) chain segments. In yet another preferred embodiment, the polynucleotide compositions have polycationic polymers having a plurality of cationic repeating units. In this case, the polynucleotides can be complexed with the polycation and stabilized in the complex. These compositions demonstrate increased permeability across cell membranes and are well suited for use as vehicles for delivering nucleic acid into cells.

In another embodiment, the invention relates to polynucleotide compositions having:

(a) a polynucleotide or derivative thereof;

(b) a block copolymer having a polyether segment and a polycation segment, wherein the polyether segment comprises at least an A-type block, and the polycation segment comprises a plurality of cationic repeating units.

In a preferred second embodiment, the copolymer relates to polymers of formulae:

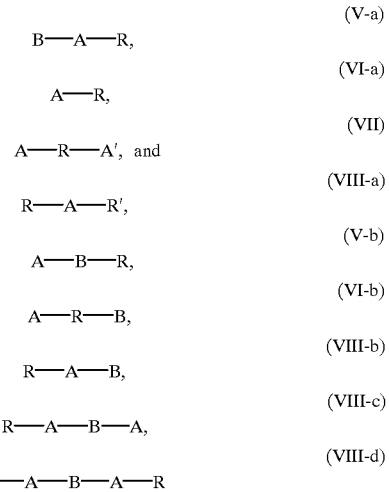

wherein A, A', and B are as described above, wherein R and R' are polymeric segments having a plurality of cationic repeating units, and each cationic repeating unit in a segment is the same or different from another unit in the segment. The polymers of this embodiment can be termed "polynonion/polycation" polymers. The R and R', blocks can be termed "R-type" polymeric segments or blocks. The polynucleotide compositions of this embodiment provide an efficient vehicle for introducing polynucleotides into a cell.

Accordingly, the invention thus further relates to methods of inserting polynucleotide into cells utilizing the compositions of the invention.

In yet another embodiment, the invention relates to polynucleotide compositions having a polynucleotide derivative comprising a polynucleotide segment and a polyether segment attached to one or both of the polynucleotide 5' and 3' ends, wherein the polyether comprises an A-type polyether segment.

In a preferred third embodiment, the derivative comprises a block copolymer of formulas:

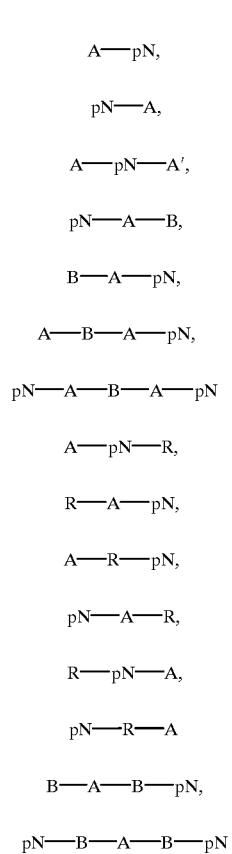

wherein pN represents a polynucleotide having 5' to 3' orientation, and A, A', and B are polyether segments as described above. In another preferred third embodiment, the polynucleotide complex comprises a polycationic polymer. The polynucleotide component (pN) of formulas (IX) through (XIII) will preferably have from about 5 to about 1,000,000 bases, more preferably about 5 to about 100,000 bases, yet more preferably about 10 to about 10,000 bases.

The polynucleotide compositions provide an efficient vehicle for introducing polynucleotides into a cell. Accordingly, the invention also relates to methods of inserting polynucleotide into cells the compositions of the invention. In another preferred embodiment, polynucleotides are covalently linked to block copolymers of poly(oxyethylene) and poly(oxypropylene).

Another embodiment of the invention relates to a polyetherpolycation copolymers having a polymer, a polyether segment, and a polycationic segment having a plurality of cationic repeating units of formula —NH—$R^0$, wherein $R^0$ is a straight chain aliphatic group of 2 to 6 carbon atoms, which may be substituted, wherein said polyether segments comprise at least one of an A-type of B-type segment. In another preferred embodiment, the polycation polymer has a polymer according to the following formulae:

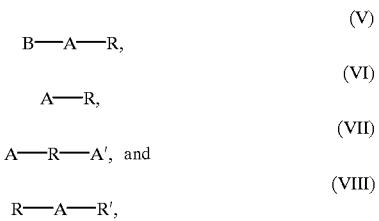

wherein A, A', and B are as described above, wherein R and R' are polymeric segments having a plurality of cationic repeating units of formula —NH—$R^0$—, wherein $R^0$ is a straight chain aliphatic group having from 2 to 6 carbon atoms, which may be substituted. Each —NH—$R^0$— repeating unit in an R-type segment can be the same or different from another —NH—$R^0$— repeating unit in the segment.

In yet another embodiment, the invention provides a polycationic polymer having a plurality of repeating units of formula:

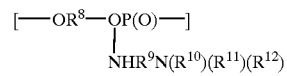

where $R^8$ is:

(1) —$(CH_2)_n$—$CH(R^{13})$—, wherein n is an integer from 0 to about 5, and $R^{13}$ is hydrogen, cycloalkyl having 3–8 carbon atoms, alkyl having 1–6 carbon atoms, or $(CH_2)_m R^{14}$, where m is an integer from 0 to about 12 and $R^{14}$ is a lipophilic substituent of 6 to 20 carbon atoms;

(2) a carbocyclic group having 3–8 ring carbon atoms, wherein the group can be for example, cycloalkyl or aromatic groups, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro, or chloro substituents; or (3) a heterocyclic group, having 3–8 ring atoms, including heterocycloalkyl or heteroaromatic groups from 1 to 4 heteroatoms selected from the group consisting of oxygen, nitrogen, sulfur and mixtures thereto, and which further can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro or chloro substituents.

$R^9$ is a straight chain aliphatic group of 1 to 12 carbon atoms, and $R^{10}$, $R^{11}$, and $R^{12}$ are independently hydrogen, an alkyl group of 1–4 carbon atoms. $R^9$ preferably is 2–10 carbon atoms, more preferably, 3–8 carbon atoms. $R^{14}$ preferably includes an intercalating group, which is preferably an acrydine or ethydium bromide group. The number of repeating units in the polymer is preferably between about 3 and 50, more preferably between about 5 and 20. This polymer structure can be incorporated into other embodiments of the invention as an R-type segment or polycationic polymer. The ends of this polymer can further be modified with a lipid substituent.

The monomers that are used to synthesize polymers of this embodiment are suitable for use as the monomers fed to a DNA synthesizer, as described below. Thus, the polymer can be synthesized very specifically. Further, the additional incorporation of polynucleotide sequences, polyether blocks, and lipophilic substituents can be done using the advanced automation developed for polynucleotide syntheses. This embodiment also encompasses the method of synthesizing a polycationic polymer.

In yet another embodiment, the invention relates to polymers having a plurality of covalently bound polymer segments wherein the segments have (a) at least one polycation segment which segment is a cationic homopolymer, copolymer, or block copolymer having comprising at least three aminoalkylene monomers, said monomers being selected from the group consisting of:

(i) at least one tertiary amino monomer of the formula:

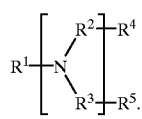

A and the quaternary salts of said tertiary amino monomer, and (ii) at least one secondary amino monomer of the formula:

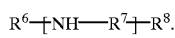

B and the acid addition and quaternary salts of said secondary amino monomer, in which:

$R^1$ is hydrogen, alkyl of 2 to 8 carbon atoms, an A monomer, or a B monomer; each of $R^2$ and $R^3$, taken independently of the other, is the same or different straight or branched chain alkanediyl group of the formula:

in which z has a value of from 2 to 8; $R^4$ is hydrogen satisfying one bond of the depicted geminally bonded carbon atom; and $R^5$ is hydrogen, alkyl of 2 to 8 carbon atoms, an A monomer, or a B monomer; $R^6$ is hydrogen, alkyl of 2 to 8 carbon atoms, an A monomer, or a B monomer; $R^7$ is a straight or branched chain alkanediyl group of the formula:

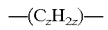

in which z has a value of from 2 to 8; and $R^8$ is hydrogen, alkyl of 2 to 8 carbon atoms, an A monomer, or a B monomer; and (b) at least one straight or branched chained polyether segment having from about 5 to about 400 monomeric units which is:

(i) a homopolymer of a first alkyleneoxy monomer —$OC_nH_{2n}$— or (ii) a copolymer or block copolymer of said first alkyleneoxy monomer and a second different alkyleneoxy monomer —$OC_mH_{2m}$—, in which n has a value of 2 or 3 and m has a value of from 2 to 4.

Polymers of formulas (I), (III), (III), or (IV) can also be mixed with each other or can be mixed either additionally or alternatively with one or more of the polymers of formula (V-a or b), (VI-a or b), (VII-a or b), and (VIII-a or b) and/or with polynucleotide derivatives of formulas (IX-a,b,c, or d), (X-a,b,c,d,e, or f), (XI), (XII) or (XIII) to provide an efficient vehicle for delivering polynucleotide to the interior of cells.

The degree of polymerization of the hydrophilic (A-type) blocks or the hydrophobic (B-type) blocks of formulas (I)–(XIII) can preferably be between about 5 and about 400. More preferably, the degree of polymerization shall be between about 5 and about 200, still more preferably, between about 5 and about 80. The degree of polymerization of the R-type polycation blocks can preferably be between about 2 and about 300. More preferably, the degree of polymerization shall be between about 5 and about 180, still more preferably, between about 5 and about 60. The degree of polymerization of the polycationic polymer can preferably be between about 10 and about 10,000. More preferably, the degree of polymerization shall be between about 10 and about 1,000, still more preferably, between about 10 and about 100.

The repeating units that comprise the blocks, for A-type, B-type and R-type blocks, will generally have molecular weight between about 30 and about 500, preferably between about 30 and about 100, still more preferably between about 30 and about 60. Generally, in each of the A-type or B-type blocks, at least about 80% of the linkages between repeating units will be ether linkages, preferably, at least about 90% will be ether linkages, more preferably, at least about 95% will be ether linkages. Ether linkages, for the purposes of this application, encompass glycosidic linkages (i.e., sugar linkages). However, in one aspect, simple ether linkages are preferred.

In yet another preferred embodiment, the compositions of the invention are useful for gene therapy purposes, including gene replacement or excision therapy, and gene addition therapy, vaccination, and any therapeutic situation in which a polypeptide should be expressed or down-regulated in the body or in vitro. In one aspect of this invention the polynucleotide compositions are used for gene therapy in muscle tissue, including but not limited to smooth, skeletal and cardiac muscles of the human or animals. It is preferred that compositions for intramuscular administration comprise the block copolymers of poly(oxyethylene) and poly(oxypropylene).

In still another preferred embodiment, the invention relates to compositions having at least one poly(oxyethylene) and poly(oxypropylene) block copolymer with oxyethylene content of 50% or less, and at least one poly(oxyethylene) and poly(oxypropylene) block copolymer with oxyethylene content of 50% or more, and a polynucleotide. The preferable ratio by weight of the block copolymer with oxyethylene content of 50% or less to the block copolymer with oxyethylene content of 50% or more is 1:2, more preferably 1:5.

It is preferred that the compositions of this invention do not form gels. The dispersions include suspensions, emulsions, microemulsions, micelles, polymer complexes, and real polymers solutions are particularly preferred. In one aspect the concentration of the polymers and block copolymers in the polynucleotide compositions is less that 10%, preferably less that 1%, more preferred less than 0.5%, yet more preferred less than 0.1%.

Block copolymers are most simply defined as conjugates of at least two different polymer segments (Tirrel, M., *Interactions of Surfactants with Polymers and Proteins*, Goddard E. D. and Ananthapadmanabhan, K. P. (eds.), CRC Press, Boca Raton, Ann Arbor, London, pp. 59–122, (1992). Some block copolymer architectures are below.

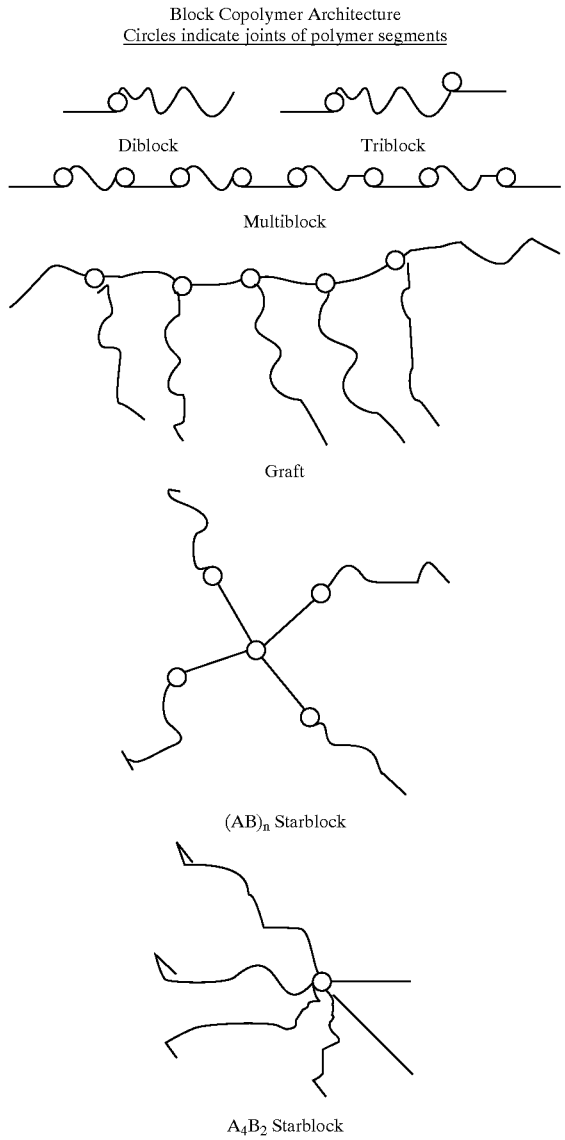

Block Copolymer Architecture
Circles indicate joints of polymer segments

Diblock    Triblock

Multiblock

Graft $(AB)_n$ Starblock $A_4B_2$ Starblock

The simplest block copolymer architecture contains two segments joined at their termini to give an A-B type diblock. Consequent conjugation of more than two segments by their termini yields an A-B-A type triblock, A-B-A-B-type multiblock, or even multisegment A-B-C-architectures. If a main chain in the block copolymer can be defined in which one or several repeating units are linked to different polymer segments, then the copolymer has a graft architecture of, e.g., an $A(B)_n$ type. More complex architectures include for example $(AB)_n$ or $A_nB_m$ starblocks which have more than two polymer segments linked to a single center.

Formulas XVIII–XXIII of the invention are diblocks and triblocks. At the same time, conjugation of polycation segments to the ends of polyether of formula XVII yields starblocks (e.g., $(ABC)_4$ type). In addition, the polyspermine of examples 13–15 (below) are branched. Modification of such a polycation with poly(ethylene oxide) yields a mixture of grafted block copolymers and starblocks. In accordance with the present invention, all of these architectures can be useful for polynucleotide delivery.

The entire disclosure of U.S. Ser. No. 08/342,079, filed, Nov. 18, 1994, now U.S. Pat. No. 5,783,178 is hereby incorporated herein by reference.

In another aspect, the invention provides a polynucleotide complex between a polynucleotide and polyether block copolymers. Preferably, the polynucleotide complex will further include a polycationic polymer. The compositions can further include suitable targeting molecules and surfactants. In another aspect, the invention provides a polynucleotide complex between a polynucleotide and a block copolymer comprising a polyether block and a polycation block. In yet another aspect, the invention provides polynucleotides that have been covalently modified at their 5' or 3' end to attach a polyether polymer segment.

Polycations. Preferred polycation polymers and polycation segments of the copolymers include but are not limited to polyamines (e.g., spermine, polyspermine, polyethyleneimine, polypropyleneimine, polybutileneimine, poolypentyleneimine, polyhexyleneimine and copolymers thereof), copolymers of tertiary amines and secondary amines, partially or completely quaternized amines, polyvinyl pyridine, and the quaternary ammonium salts of these polycation segments. These preferred polycation fragments also include aliphatic, heterocyclic or aromatic ionenes (Rembaum et al., Polymer letters, 6:159 (1968); Tsutsui, T., Development in ionic polymers-2, Wilson A. D. and Prosser, H. J. (eds.) Applied Science Publishers, London, New York, vol. 2, pp. 167–187, 1986).

The polycationic polymers and the R-type blocks have several positively ionizable groups and a net positive charge at physiologic pH. The polyether/polycation polymers of formulas (V)–(VIII) can also serve as polycationic polymers. Preferably, the polycation segments have at least about 3 positive charges at physiologic pH, more preferably, at least about 6, still more preferably, at least about 12. Also preferred are polymers or segments that, at physiologic pH, can present positive charges with a distance between the charges of about 2 Å to about 10 Å. The distances established by ethtyleneimine, aminopropylene, aminobutilene, aminopentylene and aminohehhylene repeating units, or by mixtures of at least two of these groups are most preferred. Preferred are polycationic segments that utilize ($NCH_2CH_2$), ($NCH_2CH_2CH_2$), ($NCH_2CH_2CH_2CH_2$), ($NCH_2CH_2CH_2CH_2CH_2$), and ($NCH_2CH_2CH_2CH_2CH_2CH_2$) repeating units, or a mixture thereof.

Polycation segments having an —N—$R^0$— repeating unit are also preferred. $R^0$ is preferably an ethylene, propylene, butylene, pentylene, or hexylene which can be modified. In a preferred embodiment, in at least one of the repeating units $R^0$ includes a DNA intercalating group such as an ethidium bromide group. Such intercalating groups can increase the affinity of the polymer for nucleic acid. Preferred substitutions on $R^0$ include alkyl of 1–6 carbon atoms, hydroxy, hydroxyalkyl, wherein the alkyl has 1–6 carbon atoms, alkoxy having 1–6 carbon atoms, an alkyl carbonyl group having 2–7 carbon atoms, alkoxycarbonyl wherein the alkoxy has 1–6 carbon atoms, alkoxycarbonylalkyl wherein the alkoxy and alkyl each independently has 1–6 carbon atoms, alkylcarboxyalkyl wherein each alkyl group has 1–6 carbon atoms, aminoalkyl wherein the alkyl group has 1–6 carbon atoms, alkylamino or dialkylamino where each alkyl group independently has 1–6 carbon atoms, mono- or di-alkylaminoalkyl wherein each alkyl independently has 1–6 carbon atoms, chloro, or chloroalkyl wherein the alkyl has from 1–6 carbon atoms, fluoro, or fluoroalkyl wherein the alkyl has from 1–6 carbon atoms, cyano, or cyano alkyl wherein the alkyl has from 1–6 carbon atoms or a carboxyl group. More preferably, $R^0$ is ethylene, propylene, or butylene.

The polycation polymers and polycation segments in the copolymers of the invention can be branched. For example, polyspermine-based copolymers are branched. The cationic segment of these copolymers was synthesized by condensation of 1,4-dibromobutane and N-(3-aminopropyl)-1,3-propanediamine. This reaction yields highly branched polymer products with primary, secondary, and tertiary amines.

An example of branched polycations are products of the condensation reactions between polyamines containing at least 2 nitrogen atoms and alkyl halides containing at least 2 halide atoms (including bromide or chloride). In particular, the branched polycations are produced as a result of polycondensation. An example of this reaction is the reaction between N-(3-aminiopropyl)-1,3-propanediamine and 1,4-dibromobutane, producing polyspermine.

Another example of a branched polycation is polyethyleneimine represented by the formula:

Additionally, cationic dendrimers, for example, polyamidoamines (Tomalia el al., *Angew. Chem., Int. Ed. Engl.*, 1990, 29, 138) can be also used as polycation segments of block copolymers for gene delivery.

Examples of useful polymers pursuant to formulas (V)–(VIII) include the poly(oxyethylene)-poly-L-lysine) diblock copolymer of the following formula:

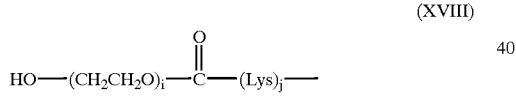
(XVIII)

wherein i is an integer of from about 5 to about 100, and j is an integer from about 4 to about 100.

A second example is the poly(oxyethylene)-poly-(L-alanine-L-lysine) diblock copolymer of formula:

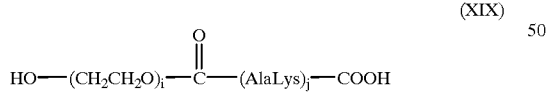
(XIX)

wherein i is an integer of from about 5 to about 100, and j is an integer from about 4 about 100.

A third example is the poly(oxyethylene)-poly (propyleneimine/butyleneimine) diblock copolymer of the following formula:

(XX)

wherein i is an integer from about 5 about 200 and j is an integer from 1 to about 10. A fourth example is the poly(oxyethylene)-poly(N-ethyl-4-vinylpyridinium bromide) ("pOE-pEVP-Br") of formula:

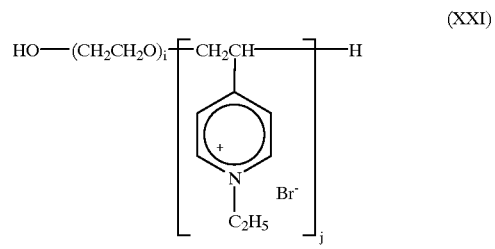
(XXI)

wherein i is an integer of from about 5 to about 100 and j is an integer of from about 10 to about 500. Still another example is the polymer of formula:

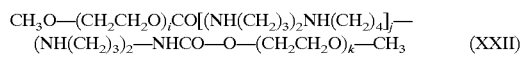
(XXII)

wherein i is an integer from about 10 to about 200, j is an integer from about 1 to about 8, and k is an integer from about 10 to about 200. Still another example is the polymer of formula:

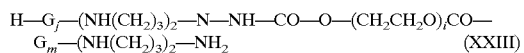
(XXIII)

wherein "G" comprises —(NH(CH$_2$)$_3$)$_3$—CH$_2$NH$_2$—, i and j are as defined for formula (XVIII), and m is an integer from about 1 to about 8.

Nonionic polyether block copolymers and nonionic polyether segments. Nonionic polyether block copolymers and polyether segments are exemplified by the block copolymers having the formulas:

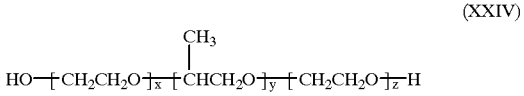
(XXIV)

(XXV)

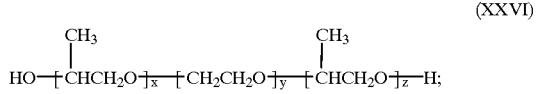
(XXVI)

-continued

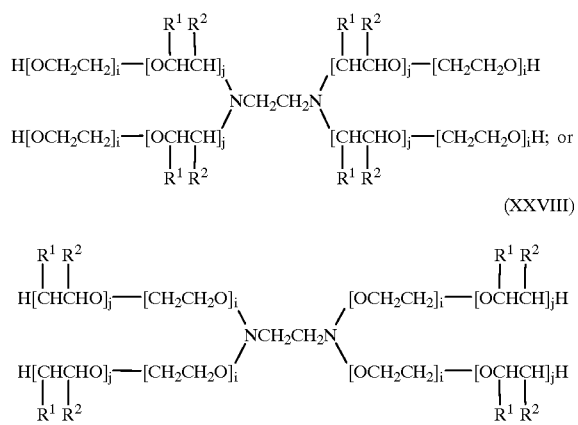
(XXVII)

(XXVIII)

in which x, y, z, i, and j have values from about 2 to about 800, preferably from about 5 to about 200, more preferably from about 5 to about 80, and wherein for each $R^1$, $R^2$ pair, one is hydrogen and the other is a methyl group. Formulas (XXIV) through (XXVI) are oversimplified in that, in practice, the orientation of the isopropylene radicals within the B block will be random. This random orientation is indicated in formulas (XXVII) and (XXVIII), which are more complete. Such poly(oxyethylene)-poly(oxypropylene) block copolymers have been described by Santon, *Am. Perfumer Cosmet.*, 72(4):54–58 (1958); Schmolka, *Loc. cit.* 82(7):25–30 (1967); *Non-ionic Surfactants*, Schick, ed. (Dekker, N.Y., 1967), pp. 300–371. A number of such compounds are commercially available under such generic trade names as "lipoloxamers", "poloxamers", "Pluronic®", and "synperonics." poly (oxyethylene)-poly(oxypropylene) polymers within the B-A-B formula are often referred to as "reversed" Pluronic®, "Pluronic-R®" or "meroxapol."

The "polyoxamine" polymer of formula (XXVII) is available from BASF (Wyandotte, Mich.) under the tradename Tetronic®. The order of the polyoxyethylene and polyoxypropylene blocks represented in formula (XXVII) can be reversed, creating Tetronic-R® of formula (XXVIII) also available from BASF. See, Schmolka, *J. Am. Oil. Soc.*, 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename Pluradot™.

A number of pluronics are designed to meet the following formula:

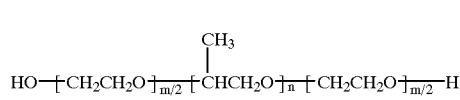
(XXIX)

Of course, those skilled in the art will recognize that the values of m and n will usually represent a statistical average and that the number of repeating units of the first block of a given molecule will generally not be exactly the number of repeating units of the third block. The characteristics of a number of block copolymers, described with reference to formula (XXIX), are as follows:

| Copolymer | MW | Average # of oxypropylene units, $n^1$ | Average # of oxyethylene units, $n^1$ | HLB | CMC, $\mu M^c$ |
|---|---|---|---|---|---|
| L31 | 1100 | 17.1 | 2.5 | 5 | 1180 |
| L35 | 1900 | 16.4 | 21.6 | 19 | 5260 |
| L43 | 1850 | 22.3 | 12.6 | 12 | 2160 |
| L44 | 2200 | 22.8 | 20.0 | 16 | 3590 |
| L61 | 2000 | 31.0 | 4.5 | 3 | 110 |
| L62 | 2500 | 34.5 | 11.4 | 7 | 400 |
| L64 | 2900 | 30.0 | 26.4 | 15 | 480 |
| F68 | 8400 | 29.0 | 152.7 | 29 | 480 |
| L81 | 2750 | 42.7 | 6.2 | 2 | 23 |
| P84 | 4200 | 43.4 | 38.2 | 14 | 71 |
| P85 | 4600 | 39.7 | 52.3 | 16 | 65 |
| F87 | 7700 | 39.8 | 122.5 | 24 | 91 |
| F88 | 11400 | 39.3 | 207.8 | 28 | 250 |
| L92 | 3650 | 50.3 | 16.6 | 6 | 88 |
| F98 | 13000 | 44.8 | 236.4 | 28 | 77 |
| L101 | 3800 | 58.9 | 8.6 | 1 | 2.1 |
| P103 | 4950 | 59.7 | 33.8 | 9 | 6.1 |
| P104 | 5900 | 61.0 | 53.6 | 13 | 3.4 |
| P105 | 6500 | 56.0 | 73.9 | 15 | 6.2 |
| F108 | 14600 | 50.3 | 265.4 | 27 | 22 |
| L121 | 4400 | 68.2 | 10.0 | 1 | 1 |
| P123 | 5750 | 69.4 | 39.2 | 8 | 4.4 |
| F127 | 12600 | 65.2 | 200.4 | 22 | 2.8 |

[1]The average numbers of oxyethylene and oxypropylene units were calculated using the average molecular weighs. The hydrophilic-lipophilic balance (HLB) of the copolymers were determined by the manufacturer (BASF Co.). The critical micellization concentrations (CMC) were determined by the surface tension method described in Kabanov et. al., Macromolecules 28: 2303–2314 (1995).

Some other specific poly(oxyethylene)-poly (oxypropylene) block copolymers relevant to the invention include:

| NN* | Block Copolymer | Hydrophobe Weight | Hydrophobe Percentage |
|---|---|---|---|
| 1 | F38 | 900 | 20% |
| 2 | L42 | 1200 | 80% |
| 3 | L63 | 1750 | 70% |
| 4 | P65 | 1750 | 50% |
| 5 | L72 | 2050 | 80% |
| 6 | F75 | 2050 | 50% |
| 7 | P77 | 2050 | 30% |
| 8 | L122 | 4000 | 80% |
| 9 | 10R5 | 1000 | 50% |
| 10 | 10R8 | 1000 | 20% |
| 11 | 12R3 | 1200 | 70% |
| 12 | 17R1 | 1700 | 90% |
| 13 | 17R2 | 1700 | 80% |
| 14 | 17R4 | 1700 | 60% |
| 15 | 17R8 | 1700 | 20% |
| 16 | 22R4 | 2200 | 60% |
| 17 | 25R1 | 2500 | 90% |
| 18 | 25R2 | 2500 | 80% |
| 19 | 25R4 | 2500 | 60% |
| 20 | 25R5 | 2500 | 50% |
| 21 | 25R8 | 2500 | 50% |
| 22 | 31R1 | 3100 | 90% |
| 23 | 31R2 | 3100 | 80% |
| 24 | 31R4 | 3100 | 60% |
| 25 | 304 | 500 | 60% |
| 26 | 504 | 1100 | 60% |
| 27 | 701 | 2200 | 90% |
| 28 | 702 | 2200 | 80% |
| 29 | 704 | 2200 | 60% |
| 30 | 707 | 2200 | 30% |

-continued

| NN* | Block Copolymer | Hydrophobe Weight | Hydrophobe Percentage |
|---|---|---|---|
| 31 | 901 | 3300 | 90% |
| 32 | 904 | 3300 | 60% |
| 33 | 908 | 3300 | 20% |
| 34 | 1101 | 4400 | 90% |
| 35 | 1102 | 4400 | 80% |
| 36 | 1104 | 4400 | 60% |
| 37 | 1107 | 4400 | 30% |
| 38 | 1301 | 5500 | 90% |
| 39 | 1302 | 5500 | 80% |
| 40 | 1304 | 5500 | 60% |
| 41 | 1307 | 5500 | 30% |
| 42 | 1501 | 7000 | 90% |
| 43 | 1502 | 7000 | 80% |
| 44 | 1504 | 7000 | 60% |
| 45 | 1508 | 7000 | 20% |
| 46 | 50R1 | 2100 | 90% |
| 47 | 50R4 | 2100 | 60% |
| 48 | 50R8 | 2100 | 20% |
| 49 | 70R1 | 3000 | 90% |
| 50 | 70R2 | 3000 | 80% |
| 51 | 70R4 | 3000 | 60% |
| 52 | 90R1 | 3900 | 90% |
| 53 | 90R4 | 3900 | 60% |
| 54 | 90R8 | 3900 | 20% |
| 55 | 110R1 | 4800 | 90% |
| 56 | 110R2 | 4800 | 80% |
| 57 | 110R7 | 4800 | 30% |
| 58 | 130R1 | 5700 | 90% |
| 59 | 130R2 | 5700 | 80% |
| 60 | 150R1 | 6700 | 90% |
| 61 | 150R4 | 6700 | 60% |
| 62 | 150R8 | 6700 | 20% |

*All block copolymers (1–8) conform to formula (XXIV), all block copolymers (9–24) conform to formula (XXVI), all block copolymers (25–45) conform to formula (XXVII), all block copolymers (46–62) conform to formula (XXVIII).

The diamine-linked block copolymer of formula (XXVII) can also be a member of the family of diamine-linked polyoxyethylene-polyoxypropylene polymers of formula:

(XXX)

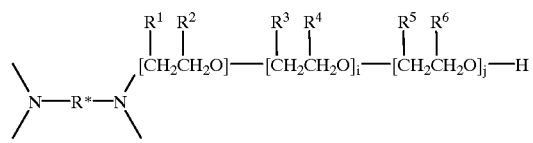

wherein the dashed lines represent symmetrical copies of the polyether extending off the second nitrogen, R* an alkylene of about 2 to about 6 carbons, a cycloalkylene of about 5 to about 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen.

The hydrophobic/hydrophilic properties of a given block copolymer depends upon the ratio of the number of oxypropylene groups to the number of oxypropylene groups. For a composition containing a single block copolymer of poly(oxyethylene)-poly(oxypropylene), for example, this relationship, taking into account the molecular masses of the central hydrophobic block and the terminal hydrophilic blocks, can be expressed as follows:

$$n = \frac{H}{L} \cdot 1.32$$

in which H is the number of oxypropylene units and L is the number of oxyethylene units. In the general case of a block copolymer containing hydrophobic B-type segments and hydrophilic A-type segments, the hydrophobic-hydrophilic properties and micelle-forming properties are related to the value n as defined as:

$$n = (|B|/|A|) \times (b/a)$$

where $|B|$ and $|A|$ are the number of repeating units in the hydrophobic and hydrophilic blocks of the copolymer, respectively, and b and a are the molecular weights for the respective repeating units.

Selecting a block copolymer with the appropriate n value will depend upon the hydrophobic/hydrophilic properties of the specific agent, or the composite hydrophilic/hydrophilic properties of a mixture of agents to be formulated. Typically, n will range in value from about 0.2 to about 9.0, more preferably between about 0.25 and about 1.5. This range should be viewed not as numerically critical but as expressing the optimum hydrophobic/hydrophilic balance between the predominantly hydrophilic poly(oxyethylene) blocks, and the predominantly hydrophobic poly(oxypropylene) blocks.

An important aspect of the present invention-involves utilizing mixture of different block-copolymers of poly(oxyethylene)-poly(oxypropylene) to achieve a more specific hydrophobic-hydrophilic balance suitable for a given cytokine or mixture of several cytokines, preserving the optimal size of particles. For example, a first block copolymer may have an n of 1.0 whereas a second may have a value of 1.5. If material having an n of 1.3 is desired, a mixture of one weight portion of the first block copolymer and 1.5 weight portion of the second block-copolymer can be employed.

Thus, a more generalized relationship for such mixtures can be expressed as follows:

$$N = 1.32 \cdot \left[ \frac{H_1 \cdot m_1}{(L_1) \cdot (m_1 + m_2)} + \frac{H_2 \cdot m_2}{(L_2) \cdot (m_1 + m_2)} \right]$$

in which $H_1$ and $H_2$ are the number of oxypropylene units in the first and second block copolymers, respectively; $L_1$ is the number of oxyethylene units in the first block copolymer; $L_2$ is the number of oxyethylene units in the second block copolymer; $m_1$ is the weight proportion in the first block-copolymer; and $m_2$ is the weight proportion in the second block copolymer.

An even more general case of a mixture of K block copolymers containing hydrophobic B-type block copolymers and hydrophilic A-type block copolymers, the N value can be expressed as follows:

$$N = \frac{b}{a} \sum_{i=1}^{k} \left( \frac{|B|_i}{|A|_i} \cdot \frac{m_i}{M} \right)$$

where $|A|_i$ and $|B|_i$ are the numbers of repeating units in the hydrophilic (A-type) and hydrophobic (B-type) blocks of the i-th block copolymer, m is the weight proportion of this block copolymers, M is the sum of weight proportions of all block copolymers in the mixture $$\left(M = \sum_{i=1}^{k} m_i\right),$$

and a and b are the molecular weights for the repeating units of the hydrophilic and hydrophobic blocks of these block copolymers respectively.

If only one block copolymer of poly(oxyethylene)-poly(oxypropylene) is utilized, N will equal n. An analogous relationship will apply to compositions employing more than two block copolymers of poly(oxyethylene)-poly(oxypropylene).

Where mixtures of block copolymers are used, a value N will be used, which value will be the weighted average of n for each contributing copolymers, with the averaging based on the weight portions of the component copolymers. The value N can be used to estimate the micelle-forming properties of a mixture of copolymers. The use of the mixtures of block copolymers enhances solubility and prevents aggregation of more hydrophobic block copolymers in the presence of the serum proteins. Particularly, poly(oxyethylene)-poly(oxypropylene) block copolymers with the ethylene oxide content of more than 50% solubilize hydrophobic block copolymers with ethylene oxide content of no more than 50%. In such mixtures, the preferred ratio of the hydrophilic and hydrophobic copolymer is at least 2:1 (w/w), preferably at least 5:1 (w/w), still more preferably at least 8:1 (w/w)." When copolymers other than polyethylene oxide-polypropylene oxide copolymers are used, similar approaches can be developed to relate the hydrophobic/hydrophilic properties of one member of the class of polymers to the properties of another member of the class.

Using the above parameters, one or more block copolymers of poly(oxyethylene)-poly(oxypropylene) are combined so as to have a value for N of from about 0.1 to about 9, more preferably from about 0.25 to about 1.5. The combined copolymers form micelles, the value of N affecting in part the size of the micelles thus produced. Typically, the micelles will have an average diameter of from about 10 to about 25 nm, although this range can vary widely. The average diameter of any given preparation can be readily determined by quasi-elastic light scattering techniques.

In another aspect, the invention relates to a polynucleotide complex comprising a block copolymer at least one of formulas (I)–(XIII), wherein the A-type and B-type blocks are substantially made up of repeating units of formula —O—$R^9$, where $R^9$ is:

(1) —$(CH_2)_n$—$CH(R^6)$, wherein n is an integer from 0 to about 5 and $R^6$ is hydrogen, cycloalkyl having 3–8 carbon atoms, alkyl having 1–6 carbon atoms, phenyl, alkylphenyl wherein the alkyl has 1–6 carbon atoms, hydroxy, hydroxyalkyl, wherein the alkyl has 1–6 carbon atoms, alkoxy having 1–6 carbon atoms, an alkyl carbonyl group having 2–7 carbon atoms, alkoxycarbonyl, wherein the alkoxy has 1–6 carbon atoms, alkoxycarbonylalkyl, wherein the alkoxy and alkyl each independently has 1–6 carbon atoms, alkylcarboxyalkyl, wherein each alkyl group has 1–6 carbon atoms, aminoalkyl wherein the alkyl group has 1–6 carbon atoms, alkylamine or dialkylamino, wherein each alkyl independently has 1–6 carbon atoms, mono- or di-alkylaminoalkyl wherein each alkyl independently has 1–6 carbon atoms, chloro, or chloroalkyl wherein the alkyl has from 1–6 carbon atoms, fluoro, fluoroalkyl wherein the alkyl has from 1–6 carbon atoms, cyano or cyano alkyl wherein the alkyl has from 1–6 carbon atoms or carboxyl; (2) a carbocyclic group having 3–8 ring carbon atoms, wherein the group can be for example, cycloalkyl or aromatic groups, and which can include alkyl having 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro or chloro substitutions, or (3) a heterocyclic group, having 3–8 ring atoms, which can include heterocycloalkyl or heteroaromatic groups, which can include from 1–4 heteroatoms selected from the group consisting of oxygen, nitrogen, sulfur, and mixtures thereof, and which can include alkyl of 1–6 carbon atoms, alkoxy having 1–6 carbon atoms, alkylamino having 1–6 carbon atoms, dialkylamino wherein each alkyl independently has 1–6 carbon atoms, amino, sulfonyl, hydroxy, carboxy, fluoro, or chloro substitutions.

Preferably, n is an integer from 1 to 3. The carbocyclic or heterocyclic groups comprising $R^5$ preferably have from 4–7 ring atoms, more preferably 5–6. Heterocycles preferably include from 1–2 hetero atoms, more preferably, the heterocycles have one heteroatom. Preferably, the heterocycle is a carbohydrate or carbohydrate analog. Those of ordinary skill will recognize that the monomers required to make these polymers are synthetically available. In some cases, polymerization of the monomers will require the use of suitable protective groups, as will be recognized by those of ordinary skill in the art. Generally, the A- and B-type blocks are at least about 80% comprised of —$OR^5$— repeating units, more preferably at least about 90%, yet more preferably at least about 95%.

In another aspect, the invention relates to a polynucleotide complex comprising a block copolymer of one of formulas (I)–(XIII) wherein the A-type and B-type blocks consist essentially of repeating units of formula —O—$R^5$ wherein $R^7$ is a C to C alkyl group.

The block copolymers utilized in the invention will typically, under certain circumstances, form micelles of from about 10 nm to about 100 nm in diameter. Micelles are supramolecular complexes of certain amphiphilic molecules that form in aqueous solutions due to microphase separation of the nonpolar portions of the amphiphiles. Micelles form when the concentration of the amphiphile reaches, for a given temperature, a critical micellar concentration ("CMC") that is characteristic of the amphiphile. Such micelles will generally include from about 10 to about 300 block copolymers. By varying the sizes of the hydrophilic and hydrophobic portions of the block copolymers, the tendency of the copolymers to form micelles at physiological conditions can be varied. The micelles have a dense core formed by the water insoluble repeating units of the B blocks and charge-neutralized nucleic acids, and a hydrophilic shell formed by the A blocks. The micelles have translational and rotational freedom in solution, and solutions containing the micelles have low viscosity similar to water. Micelle formation typically occurs at copolymer concentrations from about 0.001 to 5% (w/v). Generally, the concentration of polycationic polymers and polynucleic acid will be less than the concentration of copolymers in the polynucleotide compositions, preferably at least about 10-fold less, more preferably at least about 50-fold.

At high concentrations, some of the block copolymers utilized in the invention will form gels. These gels are viscous systems in which the translational and rotational freedom of the copolymer molecules is significantly constrained by a continuous network of interactions among copolymer molecules. In gels, microsegregation of the B block repeating units may or may not occur. To avoid the formation of gels, polymer concentrations (for both block copolymers and polyether/polycation polymers) will preferably be below about 15% (w/v), more preferably below about 10%, still more preferably below about 5%. In the first embodiment of the invention, it is more preferred that gels be avoided.

When the polynucleotide composition includes cationic components, the cations will associate with the phosphate groups of the polynucleotide, neutralizing the charge on the phosphate groups and rendering the polynucleotide component more hydrophobic. The neutralization is preferably supplied by cations on R-type polymeric segments or on polycationic polymers. However, the phosphate charge can also be neutralized by chemical modification or by association with a hydrophobic cations such as N-[1-(2,3-dioleyloxy)-N,N'-3-methylammonium chloride]. In aqueous solution, the charge neutralized polynucleotides are believed to participate in the formation of supramolecular, micelle-like particles, termed "polynucleotide complexes." The hydrophobic core or the complex comprises the charge neutralized polynucleotides and the B-type copolymer blocks. The hydrophilic shell comprises the A-type copolymer blocks. The size of the complex will generally vary from about 10 nm to about 100 nm in diameter. In some contexts, it is practical to isolate the complex from unincorporated components. This can be done, for instance, by gel filtration chromatography.

The ratio of the components of the polynucleotide composition is an important factor in optimizing the effective transmembrane permeability of the polynucleotides in the composition. This ratio can be identified as ratio Ø, which is the ratio of positively charged groups to negatively charged groups in the composition at physiological pH. If Ø<1, the complex contains non-neutralized phosphate from the polynucleotide. The portions of the polynucleotides adjacent to the non-neutralized charges are believed to be a part of the shell of a polynucleotide complex. Correspondingly, if Ø>1, the polycationic polymer or R-type segment will have non-neutralized charges, and the un-neutralized portions will fold so that they form a part of the shell of the complex. Generally, Ø will vary from about 0 (where there are no cationic groups) to about 100, preferably Ø will range between about 0.01 and about 50, more preferably, between about 0.1 and about 20. Ø can be varied to increase the efficiency of transmembrane transport and, when the composition comprises polynucleotide complexes, to increase the stability of the complex. Variations in Ø can also affect the biodistribution of the complex after administration to an animal. The optimal Ø will depend on, among other things, (1) the context in which the polynucleotide composition is being used, (2) the specific polymers and oligonucleotides being used, (3) the cells or tissues targeted, and (4) the mode of administration.

Surfactant-Containing Polynucleotide Compositions. The invention also includes compositions of polynucleotides, cationic copolymer, and a suitable surfactant. The surfactant, should be (i) cationic (including those used in various transfection cocktails), (ii) nonionic (e.g., Pluronic or Tetronic), or (iii) zwitterionic (including betains and phospholipids). These surfactants increase solubility of the complex and increase biological activity of the compositions.

Suitable cationic surfactants include primary amines, secondary amines, tertiary amines (e.g., N,N',N'-polyoxyethylene(10)-N-tallow-1,3-diaminopropane), quaternary amine salts (e.g., dodecyltrimethylammonium bromide, hexadecyltrimethylammonium bromide, mixed alkyltrimethylammonium bromide, tetradecyltrmethylammonium bromide, benzalkonium chloride, benzethonium chloride, benzyldimethyldodecylammonium chloride, benzyldimethylhexadecylammonium chloride, benzyltrimethylammonium methoxide, cetyldimethylethylammonium bromide, dimethyldioctadecyl ammonium bromide, methylbenzethonium chloride, decamethonium chloride, methyl mixed trialkyl ammonium chloride, methyl trioctylammonium chloride), N,N-dimethyl-N-[2-(2-methyl-4-(1,1,3,3-tetramethylbutyl)-phenoxy]ethoxy)ethyl]-benzenemethanaminium chloride (DEBDA), dialkyldimetylammonium salts, N-[1-(2,3-dioleyloxy)-propyl]-N,N,N,-trimethylammonium chloride, 1,2-diacyl-3-(trimethylammonio)propane (acyl group=dimyristoyl, dipalmitoyl, distearoyl, dioleoyl), 1,2-diacyl-3-(dimethylammonio)propane (acyl group=dimyristoyl, dipalmitoyl, distearoyl, dioleoyl), 1,2-dioleoyl-3-(4'-trimethylammonio) butanoyl-sn-glycerol, 1,2-dioleoyl-3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes ($C_{12}Me_6$; $C_{12}Bu_6$), dialkylglycetylphosphorylcholine, lysolecithin, L-α-dioleoyl phosphatidylethanolamine), cholesterol hemisuccinate choline ester, lipopolyamines (e.g., dioctadecylamidoglycylspermine (DOGS), dipalmitoyl phosphatidylethanolamidospermine (DPPES), lipopoly-L (or D)-lysine (LPLL, LPDL), poly(L (or D)-lysine conjugated to N-glutarylphosphatidylethanolamine, didodecyl glutamate ester with pendant amino group ($C_{12}GluPhC_nN^+$), ditetradecyl glutamate ester with pendant amino group ($C_{14}GluC_nN^+$), cationic derivatives of cholesterol (e.g., cholesteryl-3β-oxysuccinamidoethylenetrimethylammonium salt, cholesteryl-3β-oxysuccinamidoethylenedimethylamine, cholesteryl-3β-carboxyamidoethylenetrimethylammonium salt, cholesteryl-3β-carboxyamidoethylenedimethylamine, 3β[N-(N',N'-dimethylaminoetane-carbomoil]cholesterol).

Suitable non-ionic surfactants include n-Alkylphenyl polyoxyethylene ether, n-alkyl polyoxyethylene ethers (e.g., Tritons™), sorbitan esters (e.g., Spans™), polyglycol ether surfactants (Tergitol™), polyoxyethylenesorbitan (e.g., Tweens™), polysorbates, polyoxyethylated glycol monoethers (e.g., Brij™, polyoxylethylene 9 lauryl ether, polyoxylethylene 10 ether, polyoxylethylene 10 tridecyl ether), lubrol, copolymers of ethylene oxide and propylene oxide (e.g., Pluronic™, Pluronic R™, Teronic™, Pluradot™), alkyl aryl polyether alcohol (Tyloxapol™), perfluoroalkyl polyoxylated amides, N,N-bis[3-D-gluconamidopropyl] cholamide, decanoyl-N-methylglucamide, n-decyl α-D-glucopyranozide, n-decyl β-D-glucopyranozide, n-decyl β-D-maltopyranozide, n-dodecyl β-D-glucopyranozide, n-undecyl β-D-glucopyranozide, n-heptyl β-D-glucopyranozide, n-heptyl β-D-thioglucopyranozide, n-hexyl β-D-glucopyranozide, n-nonanoyl β-D-glucopyranozide 1-monooleyl-rac-glycerol, nonanoyl-N-methylglucamide, n-dodecyl α-D-maltoside, n-dodecyl β-D-maltoside, N,N-bis[3-gluconamidepropyl]deoxycholamide, diethylene glycol monopentyl ether, digitonin, heptanoyl-N-methylglucamide, heptanoyl-N-methylglucamide, octanoyl-N-methylglucamide, n-octyl β-D-glucopyranozide, n-octyl α-D-glucopyranozide, n-octyl β-D-thiogalactopyranozide, n-octyl β-D-thioglucopyranozide.

Suitable Zwitterionic surfactants include betaine ($R_1R_2R_3N^+R'CO_2^-$, where $R_1R_2R_3R'$ are hydrocarbon chains and $R_1$ is the longest one), sulfobetaine ($R_1R_2R_3N^+R'SO_3^-$), phospholipids (e.g., dialkyl phosphatidylcholine), 3-[(3-cholamidopropyl)-dimethylammonio]-2-hydroxy-1-propanesulfonate, 3-[(3-cholamidopropyl)-dimethylammonio]-1-propanesulfonate, N-decyl-N,N-dimethyl-3-ammonio-1-propanesulfonate, N-dodecyl-N,N-dimethyl-3-ammonio-1-propanesulfonate, N-hexadecyl-N,N-dimethyl-3-ammonio-1-propanesulfonate, N-octadecyl-N,N-dimethyl-3-ammonio-1-propanesulfonate, N-octyl-N,N-dimethyl-3-ammonio-1-propanesulfonate, N-tetradecyl-N,N-dimethyl-3-ammonio-1-propanesulfonate, and dialkyl phosphatitidylethanolamine.

Nucleic acids. A wide variety of nucleic acid molecules can be the nucleic acid component of the compositions. These include natural and synthetic DNA or RNA molecules and nucleic acid molecules that have been covalently modified (to incorporate groups including lipophilic groups, photo-induced crosslinking, groups, alkylating groups, organometallic groups, intercalating groups, lipophilic groups, biotin, fluorescent, and radioactive groups, and groups that modify the phosphate backbone). Such nucleic acid molecules can be, among other things, antisense nucleic acid molecules, gene-encoding DNA (usually including an appropriate promoter sequence), ribozymes, aptamers, anitgen nucleic acids, oligonucleotide α-anomers, ethylphosphotriester analogs, alkylphosphomates, phosphorothionate and phosphorodithionate oligonucleotides, and the like. In fact, the nucleic acid component can be any nucleic acid that can beneficially be transported into a cell with greater efficiency, or stabilized from degradative processes, or improved in its biodistribution after administration to an animal.

Targeting molecules. It will in some circumstances be desirable to incorporate, by noncovalent association, targeting molecules. See for example, Kabanov et al., *J. Controlled Release*, 22:141 (1992), the contents of which are hereby incorporated by reference. The targeting molecules that can be associated with the composition typically have a targeting group having affinity for a cellular site and a hydrophobic group. The targeting molecule will spontaneously associate with the polynucleotide complex and be "anchored" thereto through the hydrophobic group. These targeting adducts will typically comprise about 10% or less of the copolymers in a composition.

In the targeting molecule, the hydrophobic group can be, among other things, a lipid group such as a fatty acyl group. Alternately, it can be a block copolymer or another natural synthetic polymer. The targeting group of the targeting molecule will frequently comprise an antibody, typically with specificity for a certain cell surface antigen. It can also be, for instance, a hormone having a specific interaction with a cell surface receptor, or a drug having a cell surface receptor. For example, glycolipids could serve to target a polysaccharide receptor. It should be noted that the targeting molecule can be attached to any of the polymer blocks identified herein, including R-type polymeric blocks and to the polycationic polymers. For instance, the targeting molecule can be covalently attached to the free-terminal groups of the polyether segment of the block copolymer of the invention. Such targeting molecules can be covalently attached to the —OH end group of the polymers of the formulas XVIII, XIX, XX, and XXI, and the —NH$_2$ end group of the polymers of formulas XVIII (preferably the ε-amino group of the terminal lysyl residue), XX or XXIII, or the —COOH end group of the polymers of formulas XVIII and XIX. Targeting molecules can be used to facilitate intracellular transport of the polynucleotide composition, for instance transport to the nucleus, by using, for example, fusogenic peptides as targeting molecules described by Soukchareun et al., *Bioconjugate Chem.*, 6:43 (1995), or Arar et al., *Bioconjugate Chem.*, 6:43 (1995), caryotypic peptides, or other biospecific groups providing site-directed transport into a cell (in particular, exit from endosomic compartments into cytoplasm, or delivery to the nucleus).

The polynucleotide component of the compositions can be any polynucleotide, but are preferably a polynucleotide with at least about 3 bases, more preferably at least about 5 bases. Still more preferred are at least 10 bases. Included among the suitable polynucleotides are viral genomes and viruses (including the lipid or protein viral coat). This includes viral vectors including, but not limited to, retroviruses, adenoviruses, herpes-virus, or Pox-virus. Other suitable viral vectors for use with the present invention will be obvious to those skilled in the art. The terms "poly (nucleic acid)" and "polynucleotide" are used interchangeably herein. An oligonucleotide is a polynucleotide, as are DNA and RNA.

A polynucleotide derivative is a polynucleotide having one or more moieties (i) wherein the moieties are cleaved, inactivated or otherwise transformed so that the resulting material can function as a polynucleotide, or (ii) wherein the moiety does not prevent the derivative from functioning as a polynucleotide.

Therapeutic applications. The present compositions can be used in a variety of treatments. For example, the compositions can be used in gene therapy including gene replacement or excision therapy, and gene addition therapy (B. Huber, Gene therapy for neoplastic diseases; B. E. Huber and J. S. Lazo Eds., The New York Academy of Sciences, N.Y., N.Y., 1994, pp. 6–11). Also, antisense therapy targets genes in the nucleus and/or cytoplasm of the cell, resulting in their inhibition (Stein and Cheng, Science 261:1004 (1993); De Mesmaeker et al., *Acc. Chem. Res.*, 28:366 (1995)). Aptamer nucleic acid drugs target both intra-and extracellular proteins, peptides and small molecules. See Ellington and Szostak, *Nature* (London), 346:818 (1990). Antigen nucleic acid compounds can be used to target duplex DNA in the nucleus. See Helene and Tolume, *Biochim, Biophys.*, Acta 1049:99 (1990). Catalytic polynucleotides target mRNA in the nucleus and/or cytoplasm. Cech, *Curr. Opp. Struct. Biol.*, 2:605 (1992).

Examples of genes to be replaced, inhibited and/or added include, adenosine deaminase, tumor necrosis factor, cell growth factors, Factor IX, interferons (such as α-, β-, and γ-interferon), interleukins (such interleukin 2, 4, 6, and 12), HLA-B7, HSV-TK, CFTR, HIV-1, β-2, microglobulin, retroviral genes (such as gag, pol, env, tax, and rex), cytomegalovirus, herpes viral genes (such as herpes simplex virus type I and II genes ICP27/UL54, ICP22/US1, ICP/IE175, protein kinase and exonuclease/UL13, protein kinase/US3, ribonuclease reductase ICP6/UL39, immediate early (IE) mRNA IE3/IE175/ICP4, 1E4/ICP22/US1, IE5/ICP47, IE110, DNA polymerase/UL30, UL13), human multidrug resistance genes (such as mdrl), oncogenes (such as H-c-ras, c-myb, c-myb, bcl-2, bcr/abl), tumor suppressor gene p53, human MHC genes (such as class 1 MHC), immunoglobulins (such as IgG, IgM, IgE, IgA), hemoglobin α- and β-chains, enzymes (such as carbonic anhydrase, triosephoshate isomerase, GTP-cyclhydrdolase I, phenylalanine hydrolase, sarcosine dehydrogenase, glucocerobrosidase, glucose-6-phosphste dehydrogenase), dysotrophin, fibronectin, apoliprotein E, cystic fibrosis transmembrane conductance protein, c-src protein, V(D)J recombination activating protein, immunogenes, peptide and protein antigens ("DNA vaccines") and the like.

Genetic diseases can also be treated by the instant compositions. Such diseases include, rheumatoid arthritis, psoriasis, Crohn's disease, ulcerative colitis, α-thalassemia, β-thalassemia, carbonic anhydrase II deficiency syndrome, triosephosphate isomerase deficiency syndrome, tetrahydrobiopterindeficient hyperphenylalaniemia, classical phenylketonuria, muscular dystrophy such as Duchenne Muscular Dystrophy, hypersarkosinemia, adenomatous intestinal polyposis, adenosine deaminase deficiency, malignant melanoma, glucose-6-phosphste dehydrogenase deficiency syndrome, arteriosclerosis and hypercholesterolemia, Gaucher's disease, cystic fibrosis, osteopetrosis, increased spontaneous tumors, T and B cell immunodeficiency, high cholesterol, arthritis including chronic rheumatoid arthritis, glaucoma, alcoholism and the like.

The compositions can also be used to treat neoplastic diseases including, but not limited to, breast cancer (e.g., breast, pancreatic, gastric, prostate, colorectal, lung, ovarian), lymphomas (such as Hodgkin and non-Hodgkin lymphoma), melanoma and malignant melanoma, advanced cancer hemophilia B, renal cell carcinoma, gliblastoma, astrocytoma, gliomas, AML and CML and the like.

Additionally, the compositions can be used to treat (i) cardiovascular diseases including but not limited to stroke, cardiomyopathy associated with Duchenne Muscular Dystrophy, myocardial ischemia, restenosis and the like, (ii) infectious diseases such as Hepatitis, HIV infections and AIDS, Herpes, CMV and associated diseases such as CMV renitis, (iii) transplantation related disorders such as renal transplant rejection and the like, and (iv) are useful in vaccine therapies and immunization, including but not limited to melanoma vaccines, HIV vaccines, malaria, tuberculosis, and the like.

Target Cells. Cell targets can be ex vivo and/or in vivo, and include T and B lymphocytes, primary CML, tumor infiltrating lymphocytes, tumor cells, leukemic cells (such as HL-60, ML-3, KG-1 and the like), skin fibroblasts, myoblasts, cells of central nervous system including primary neurons, liver cells, carcinoma (such as Bladder carcinoma T24, human colorectal carcinoma Caco-2), melanoma, CD34+ lymphocytes, NK cells, macrophages, hemotopoetic cells, neuroblastona (such as LAN-5 and the like), gliomas, lymphomas (such as Burkitt lymphomas ST486), JD38), T-cell hybridomas, muscle cells such as primary smooth muscle, and the like.

Methods of use. The polynucleotide compositions of the invention can be administered orally, topically, rectally, vaginally, by pulmonary route by use of an aerosol, or parenterally, i.e. intramuscularly, subcutaneously, intraperitoneallly or intravenously. The polynucleotide compositions can be administered alone, or it can be combined with a pharmaceutically-acceptable carrier or excipient according to standard pharmaceutical practice. For oral administration, the polynucleotide compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the polynucleotide compositions can be combined with emulsifying and suspending agents. If desired, sweetening and/or flavoring agents can be added. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly (vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

For intramuscular administration, the formulation of the polynucleotides will be without any polycationic moiety since naked polynucleotides itself can be transferred and expressed in muscle without any polycation-containing delivery systems. The muscle has the following features: unique cytoarchitecture, multiple nuclei per myotubes, specific-polynucleotides binding proteins (triadin), and unique nucleocytoplasmic transport. At present, it is still unclear as to which features listed above may be responsible for the uptake and expression of naked polynucleotides in muscle. Cationic complexes of polynucleotides have been shown to enhance uptake and gene expression in virtually all tissue types but surprisingly the same complexes do not contribute to a better uptake and gene expression in muscle. In fact, cationic complexation of polynucleotides inhibit uptake and gene expression in muscle and reported by several laboratories. Thus, for intramuscular injection of polynucleotides, complexation of polynucleotides should be avoided. This invention uses nonionic block copolymers for intramuscular delivery of polynucleotides. Block copolymers alone are totally inefficient at transferring genetic material in cells in vitro and in vivo (see example 42). Moreover, unlike polycation-containing block copolymers, the above nonionic block copolymers do not increase gene expression in the peripheral organs such as lungs, liver, kidneys.

The following examples will serve to further typify the nature of the invention but should not be construed as a limitation on the scope thereof, which is defined solely by the appended claims.

EXAMPLE 1

Transfection Efficiencies

This experiment introduced plasmid pβ-Gal into NIH 3T3 cells, a mouse mammary tumor cell line. Plasmid pβ-Gal comprises plasmid pUC19 (available from the Institute of Gene Biology, Russian Academy of Sciences) into which a hybrid of a eukaryotic transcription unit and a *E. coli* β-galactosidase has been incorporated. With this plasmid, the efficiency of cell uptake can be measured by measuring β-galactosidase activity extractable from the treated cells. The copolymer utilized was a triblock copolymer of formula (XIV) wherein x plus z was 51 and y was 39 (hereinafter "Pluronic A"). The polycation used was poly(N-ethyl-4-vinylpyridinium bromide) ("pEVP-Br"). A 10 µg/ml solution of pβ-Gal (predominantly supercoiled) was prepared in a solution of PBS containing 10 mg/ml of Pluronic A and 45 µg/ml of pEVP-Br. These amounts were calculated to provide a ratio of polycation basic groups to plasmid phosphate groups of about 10. The ratio of Pluronic A to DNA was about $10^4$. This stock preparation was filter sterilized and a portion was diluted ten fold with serum-free Dulbecco's Modified Eagle's Medium ("DMEM"), so that the concentration of pβ-Gal was 1 μg/ml. This solution was the "Pluronic A transfecting medium."

The NIH 3T3 cells were grown in monolayer culture at 37° C. under 5% $CO_2$, using a DMEM medium containing 2 mM glutamine and 10% fetal calf serum ("FCS"). Cells were grown in monolayer culture were scraped and prepared for the transaction process by washing three times with fresh medium.

Aliquots of washed cells that were to be transformed by the method of the invention were suspended at a concentration of $10^6$ cells/ml in Pluronic A transfecting medium. The suspended cells were incubated for 2 hours at 37° C. and under 5% $CO_2$. The cells were then washed with fresh medium and re-plated.

Aliquots of cells that were to be transfected by calcium phosphate precipitation were transfected as recommended by Promega of Madison, Wis., in their manuscript *Profection Mammalian Transfection Systems*, Technical Manual, 1990. Specifically, pβ-Gal was mixed with 0.25M $CaCl_2$. The mixture was mixed with an equal volume of 2×HBS (Hanks Buffer Salt, available from GIBCO, Grand Island, N.Y.) to create a mixture containing 1 μg/mL pβ-Gal. The opaque mixture was incubated at room temperature for 10 minutes and then applied to the cells. The suspended cells were incubated for 2 hours at 37° C. and under 5% $CO_2$. The cells were then washed with fresh medium and re-plated.

The repeated cells were incubated for 48 hours in DMEM medium containing 10% FCS. During the incubation, the medium was replaced with fresh medium at 16 hours. After the 48 hour incubation, the cells for each incubation were collected by scrapping, washed with PBS, and resuspended in 100 μl of 0.2 M Tris-HCL (pH 7.4). The cells were lysed with several freeze/thaw cycles, and centrifuged at an excess of 6,000×/g. 50 μl of supernatant was removed from each lysate tube and mixed with 50 μl of a solution of 0.1 mM 4-methyl-umbelliferril-β-D-galactopiraniside (the substrate), 0.1 M sodium phosphate (pH 7.4). Each mixture was incubated for 20 min. at 37° C. to allow any β-galactosidase present to act on the substrate. 50 μl of 0.4 M glycine, pH 10.5, was added to terminate the β-galactosidase reaction. β-galactosidase activity was indicated by the presence of methylbelliferon, which can be measured by fluorescence spectroscopy ($\lambda_{ex}$=365 nm, $\lambda$=450 nm). The results were as follows:

| Treatment | Relative Enzyme Activity ± SEM (n = 4) |
|---|---|
| Pluronic A | 320 ± 42 |
| Calcium Phosphate Precipitation | 17 ± 5 |

EXAMPLE 2

Transfection Efficiencies

In these experiments, transfection efficiencies with MDCK cells (derived from canine kidney) were examined. As above, pβ-Gal was the indicator polynucleotide. The polycation component of the polynucleotide comprised a copolymer of N-ethyl-4-vinylpyridinium bromide and N-cetyl-4-vinylpyridinium bromide, the monomers incorporated in a molar ratio of 97:3, respectively (hereinafter "pEVP-co-pCVP-Br"). The block copolymer comprised a triblock copolymer of formula (XIV) wherein x+z was 18, and y was 23 (hereinafter "Pluronic B"). A Pluronic B transfecting solution of 1 μg/ml pβ-Gal, 3 μg/ml PEVPco-pCVP-Br, and 1% (w/v) Pluronic B was prepared in Example 1. The ratio of polycation basic groups to nucleotide Phosphates was about 7. The weight ratio of Pluronic B to pβ-Gal was about 5×$10^3$.

MDCK cells were plated at 8–$10^5$ cells per plate onto 90 mm plates and incubated overnight under serum-containing growth medium. The serum containing medium was then replaced with serum-free medium, and the cells were incubated at 37° C., under 5% $CO^2$ for 24 hours. For the cells to be treated with polynucleotide complex, the medium was then replaced with 5 ml Pluronic B transfecting solution. The cells were incubated, with gentle rocking, at 37° C., under 5% $CO_2$ In control experiments, cells were transfected with polynucleotide complex, the medium was then replaced with 5 ml Pluronic B transfecting solution. The cells were incubated, with gentle rocking, at 37° C., under 5% $CO_2$, for 2 hours. In control experiments, cells were transfected using the calcium phosphate procedure as described above (except that plated cells, not suspended cells, were transfected).

After treatment with Pluronic B transfecting solution or calcium phosphate, the cells were washed 5–6 times with fresh medium. They were then incubated in DMEM containing 10% FCS for 48 hours at 37° C., under 5% $CO_2$. After the first 16 hours of this incubation, the medium was replaced. After the incubation, the cells were washed with PBS, released from their plates by trypsinization, and again washed with PBS. β-Galactosidase was measured as described for Example 1. The results were as follows:

| Treatment | Relative β-galactosidase activity ± SEM (n = 4) |
|---|---|
| Pluronic B | 910 ± 45 |
| Calcium Phosphate Precipitation | 81 ± 17 |

EXAMPLE 3

Transfection Experiments

In these experiments, transfection efficiencies with Chinese hamster ovary (CHO) cells were examined. The polynucleotic component of the polynucleotide complex was pβ-Gal. The polycation component comprised pEVPBr. The block copolymer comprised an octablock copolymer formula (XVII), wherein i was equal to 10 and j was equal to 12 (hereinafter "Pluronic C" available from BASF). A Pluronic C transfecting solution of 1 μg/ml pβ-Gal, 4 μg/ml pEVP-Br, and 1% (w/v) Pluronic C was prepared as in Example 1. The ratio of basic groups to nucleotide phosphates was 10. The weight ratio of Pluronic C to pβ-Gal was $10^3$. The transfection protocol was the same as that used in Example 2. The results were as follows:

| Treatment | Relative β-galactosidase activity ± SEM (n = 4) |
|---|---|
| Pluronic B | 910 ± 45 |
| Calcium Phosphate Precipitation | 81 ± 17 |

EXAMPLE 4

Bacterial Transformation

In these experiments, transformation efficiencies using the MC5 strain of *Bacillus subtilis* were examined. The polynucleotide component of the polynucleotide complex was plasmid pBC16, a plasmid encoding tetracycline resistance. A block copolymer according to formula (VI) was used. In particular, the block copolymer was a poly(oxyethylene)-oly((N-ethyl-4-vinylpyridinium bromide) of formula (XXI), wherein i was 44, and j was 20. A stock solution of second embodiment polynucleotide complex was prepared consistent with the transfection solutions described above. The ratio of copolymer basic groups to DNA phosphates in the solution was 0.2. Bacteria were suspended in Spizizen 11, a transformation media (see, Spizizen, F.N.A.S., U.S.A. 44:1072 (1958)), and aliquots of cells were incubated in varying concentrations of either polynucleotide complex or free pBC16. The cells were incubated with complex or free DNA for one hour at 37° C. Following the incubation, the cells were plated onto agar media containing 10 mg/ml tetracycline. The results, measured by the number of tetracycline-resistant colonies produced under each of the experimental conditions, were as follows:

| DNA | Transformation ($10^6$ clones/ng DNA) | |
| --- | --- | --- |
| concentration (ng/ml) | Polynucleotide Complex | Free Polynucleotide |
| 5 | 300 (±15) | 0 |
| 10 | 450 (±22) | 3 (±1) |
| 20 | 400 (±26) | 3 (±4) |
| 50 | 220 (±17) | 20 (±5) |

EXAMPLE 5

Protection from Nuclease

For this example, a complex of plasmid pTZ19 and a diblock copolymer of formula (XXI) (poly(oxyethylene)-poly((N-ethyl-4-vinylpyridinium bromide), wherein i was 44 and j was 20) was formed. The solution of polynucleotide complex dissolved in PBS contained about 4 µg/ml of plasmid and 20 µg/ml of diblock copolymer. These amounts resulted in a ratio of base groups in the polycation block to DNA phosphate groups of 5. For control incubations, an equivalent amount of free plasmid was dissolved in buffer. PVUII nuclease was added to solution samples containing free DNA or polynucleotide complex, and the amount of undigested, circular plasmid DNA, after various digestion times, was determined by electrophoresis in a polyacrylamide gel. See Kabanov et al., *Biopolymers*, 31:1437–1443 (1991). The results were as follows:

| | Circular DNA (% of initial) | |
| --- | --- | --- |
| Time of Incubation | Complex | Free DNA |
| 0 | 100 | 100 |
| 5 | 100 | 20 |
| 10 | 100 | 8 |
| 30 | 100 | 4 |
| 60 | 100 | 1 |
| 180 | 100 | 0 |
| 600 | 100 | 0 |

EXAMPLE 6

Oligonucleotide Stabilization

For this example, a complex containing an oligonucleotide complementary to the transcription initiation site of the HIV-1 tat gene ("anti-tat", comprising GGCTCCATTTCTTGCTC) was prepared using the diblock copolymer of formula (XIX) (polyoxyethylene-poly(L-alanine-L-lysine), wherein i is 44 and j is 8). The oligonucleotide complex was prepared in PBS Buffer (pH 7.0) at a concentration of 0.75 $OD_{260}$/µl oligonucleotide. The ratio of polycation imino and amino groups to polynucleotide phosphate groups was about 50. The mixture was incubated for one hour at room temperature to allow for the formation of the complex. Then, the complex was purified by gel filtration chromatography on Sephadex G-25 using 0.05 M NaCl as the eluent. The resulting solution of complex exhibited a concentration of 0.11 $OD_{260}$/µl of oligonucleotide. A comparable solution of uncomplex oligonucleotide was prepared. An aliquot of murine blood plasma (10 µl) was mixed with an equal volume of oligonucleotide complex solution or a solution of free oligonucleotide. Samples were incubated at 37° C. for various time periods. To stop the reaction of the oligonucleotides with enzymes in the plasma, the samples were diluted with water and extracted with a water-saturated mixture of phenol:chloroform (1:1). The aqueous phase of the extraction was isolated, and the oligonucleotide therein was precipitated with 3% lithium Perchlorate. The precipitate was washed with acetone, and then dissolved in 100 µl of water. The presence of undergraded oligonucleotide was determined by high performance liquid chromatography using a $C_{18}$-Silasorb column (4×90 mm, Gilson, France) and a gradient of acetonitrile in 0.05 M triethylammoniumacetate (pH 7.0) as the eluent. The results were as follows:

| Time of | Undergraded oligonucleotide (%) | |
| --- | --- | --- |
| Incubation | Complex | Free Oligo |
| 0 | 100 | 100 |
| 3 hours | 88 | 28 |
| 6 hours | 70 | 17 |
| 24 hours | 36 | 0 |

EXAMPLE 7

Oligonucleotide Stabilization

This example examined the stability of the oligonucleotide described in Example 6, when complexed with a diblock copolymer of formula (XX) (polyoxyethylene-polypropyleneimine/butyleneimine, wherein i is 44 and j is 4–8) was examined. The same methodologies that were applied in Example 6 were applied for this example, except that the oligonucleotide concentration was about 0.13 $OD_{260}$/µl. The results were as follows:

| Time of | Undergraded oligonucleotide (%) | |
| --- | --- | --- |
| Incubation | Complex | Free Oligo |
| 0 | 100 | 100 |
| 3 hours | 70 | 28 |
| 6 hours | 57 | 17 |
| 24 hours | 28 | 0 |

EXAMPLE 8

Antisense Cell Incorporation Efficiencies

This experiment examined the effectiveness of "anti-MDR", an antisense molecule comprising a 17-chain oligonucleotide of sequence CCTTCAAGATCCATCCC complementary to positions 422–438 of the mRNA encoding the MDR1 gene product, in reversing multi-drug resistance in SKVLB cells. SKVLB cells are multi-drug resistant cells derived from a ovarian cancer cell line. The MDR1 gene has been identified as responsible for the multi-drug resistance in SKVLB cells. Endicott and Ling, *Ann. Rev. Biochem.*, 58:137 (1989). In particular, the efficiency of the anti-MDR oligonucleotide in the polynucleotide complex of the invention and when in the free state was compared. As controls, the free and completed form of the anti-tat oligonucleotide described above were also used. The polynucleotide complexes were formed with the diblock copolymer of formula (XX) (polyoxyethylenepolypropyleneimine/butyleneimine, where i was 44 and j was 9–10). The complexes were prepared by the procedures described in Example 6. The oligonucleotide concentration in the complex or in the free state was 0.17 $OD_{260}/\mu l$. The copolymer was present in the concentration sufficient to define a ratio of polycation block imino and amino groups to oligonucleotide phosphate groups of 10.

The SKVLB cells were incubated for 3 days at 37° C. under 5% $CO_2$ in the presence of free or completed oligonucleotide (at a concentration of 20 $\mu M$ based on oligonucleotide content). Fresh media including free or completed oligonucleotide was added every 12 hours.

The daunomycin cytotoxicity ($IC_{50}$) with respect to the cells treated as described above was measured using the method of Alley et. al., *Cancer Res.*, 48:589–601. The results were as follows:

| Treatment of Cells | Daunomycin $IC_{50}$ (ng/ml) (n = 4) |
|---|---|
| Control (untreated cells) | 8.0 |
| Anti-MDR Complex | 0.3 |
| Anti-tat Complex | 8.2 |
| Free Anti-MDR | 2.1 |
| Free Anti-tat | 7.9 |

EXAMPLE 9

Antisense Oligonucleotide Designed to Inhibit Herpes Virus

This experiment used a 12-chain oligonucleotide, which had been covalently modified at its 5' end with undecylphosphate substituent and at is 3' end with a acridine group, was used. This olgonucleotide modification has been described by Cho-Chung et. al., *Biochemistry Int.*, 25:767–773 (1991). The oligonucleotide sequence utilized, CGTTCCTCCTGU, was complementary to the splicing site at 983–994 of the Herpes Simplex Virus 1 ("HSV-1"). As a control, an equivalently modified sequence (AGCAAAAGCAGG) complementary to the RNA produced by influenza virus was utilized. The oligonucleotides were applied to HSV-1 infected cells in either the complexed or the free state. When a complex was utilized, the complex was formed with the diblock copolymer of formula (XIX) (polyoxyethylene-poly (L-alanine-L-lysine), wherein i was equal to 44 and j was equal to 8). Oligonucleotide complexes were formed as described in Example 6.

African marmoset kidney cells ("Vero" cells) were infected with HSV-1 virus (strain L2, obtained from the Museum of Virus Strains, D. I. Ivanovskii, *Inst. of Virol.*, Russian Federation), as described by Vinogradov et al., *BBRC*, 203:959 (1994). The infected cells were washed with PBS. After washing, fresh RPMI-L 640 media containing 10% of fetal calf serum and free or complex oligonucleotide was added to the cell. The cells were then incubated at 37° C. under 5% $CO_2$ for 24 hours. The HSV-1 infectivity of the cell media was then determined using the patch production method described by *Virology, A Practical Approach*, Mahy, Ed., IRL Press, Washington, D.C., 1985. The results, utilizing varying concentrations of oligonucleotide, were as follows:

| Oligo Conc. | HSV-1 Infectious Titre ($CPE_{50}$/ml) (n=7) | | |
|---|---|---|---|
| Treatment | 0.2 $\mu M$ | 1.0 $\mu M$ | 5.0 $\mu M$ |
| Control (untreated infected cells) | 1.0 (±0.5) × $10^6$ | 1.0 (±0.5) × $10^6$ | 1.0 (±0.5) × $10^6$ |
| Anti-HSV complex | 1.4 (±0.2) × $10^2$ | 0.5 (±0.3) × $10^2$ | 0 |
| Anti-influenza complex | 1.0 (±0.6) × $10^6$ | 0.7 (±0.1) × $10^6$ | 0.8 (±0.2) × $10^6$ |
| Free Anti-HSV | 0.9 (±0.4) × $10^5$ | 2.3 (±0.7) × $10^3$ | 1.6 (±0.4) × $10^2$ |
| Free Anti-Influenza | 1.1 (±0.4) × $10^6$ | 0.9 (±0.2) × $10^6$ | 0.6 (±0.3) × $10^6$ |

EXAMPLE 10

Antisense Oligonucleotide Designed to Inhibit Herpes Virus

Unless otherwise noted, this example utilized the same procedures as were utilized in Example 9. The cells utilized were BHK cells, a Chinese hamster kidney cell line. When the complexed form of the oligonucleotides was used, the complex was formed with the diblock copolymer of formula (XVII) (polyoxyethylene-poly-L-lysine, wherein i was 44 and j was 30), using the procedure described in Example 6. The concentration of the stock solution of complex was 0.09 $OD_{260}/\mu l$. The ratio of polycation block imino and amino groups to oligonucleotide phosphates was 10. The oligonucleotides, in complexed or free form, were applied to the cells at a concentration of 3.0 $\mu M$. The results were as follows:

| Treatment of cells | HSV-1 infectious titre ($CPE_{50}$/ml) n = 7 |
|---|---|
| Control (untreated infected cells) | 10(±3) × $10^3$ |
| Anti-HSV complex | 8(±6) |
| Anti-influenza complex | 13(±4) × $10^3$ |
| Free Anti-HSV | 50(±14) × $10^2$ |
| Free Anti-influenza | 9(±2) × $10^3$ |

EXAMPLE 11

In Vivo Inhibition of HSV

Polynucleotide complexes between the block copolymer of formula (XVII) (polyoxyethylenepoly-L-lysine, wherein i was 44 and j was 30) and the Anti-HSV and Anti-Influenza oligonucleotides were formed using the methods outlined in Example 9. The concentration of the stock solutions of complexes was 0.9 $OD_{260}/\mu l$. The ratio of polycation block imino and amino groups to oligonucleotide phosphates was 10.

Inbred white mice (body weight 6–7 g) were infected with HSV-1 (strain C1 from *Belorussian Res. Inst. of Epidemiol.*

& *Microbiol., Minsk*) by intraperitoneal injection of 30 μl of a virus suspension (titre: $10^{-7}$ $LD_{50}$/ml).

Either Anti-HSV complex, Anti-influenza complex, free Anti-HSV or free Anti-Influenza were injected (10 μl) into the tail vein of a given mouse at each of 2, 12, 24, 48, or 72 hours post-infection. The results were as follows:

| Treatment of mice | Survived animals/Amount of Animals in a group | | | % Survival |
|---|---|---|---|---|
| | Exp. 1 | Exp. 2 | Exp. 3 | |
| Control (infected mice) | 1/9 | 1/10 | 2/10 | 13.7 |
| Anti-HSV complex | 8/9 | 6/10 | 7/10 | 73.0 |
| Anti-influenza complex | 2/10 | 0/10 | 1/10 | 10.0 |
| Free Anti-HSV | 1/10 | 1/10 | 0/10 | 7.0 |
| Free Anti-influenza | 0/9 | 1/10 | 0/10 | 7.0 |

EXAMPLE 12

Plasma Life of Polynucleotide Complex

A $^{32}$P-labelled 17-mer (GGCTCCATTTCTTGCTC) complementary to the transcription initiation site of the HIV-1 tat gene was utilized in this example. The oligonucleotide was modified at its 5'-end with cholesterol as described by Boutorin et al., *Bioconjugate Chemistry*, 2: 350–356 (1990). A polynucleotide conjugate of the oligonucleotide was formed with the block copolymer of formula (XX) polyoxyethylene-poly(propyleneimine/butyleneimine), wherein i was 44 and j was 9 to 10). The concentration of the stock solution (dissolved in PBS) of complex was 0.18 $OD_{260}$/μl. The ratio of polycation block imino and amino groups to oligonucleotide phosphates was 50.

Male C57/B1/6 mice (weight: 20–24 g; obtained from the Russian Research Center of Molecular Diagnostics and Therapy, Moscow) received 50 μl intravenous injections of Anti-HIV conjugate or free Anti-HIV, at 0.18 $OD_{260}$/μl dissolved in PBS. At defined times after the injections, blood sample were taken from the tail vein and the animals were sacrificed. The amount of radioactive material in blood or tissue sample was determined by liquid scintillation counting (after appropriate solubilizations). The results were as follows:

| Time after injection (min) | Plasma levels (% of injected dose) | | Liver levels (% of injected dose) Prep. A | Liver levels (% of injected dose) Prep. B |
|---|---|---|---|---|
| | Anti-HIV Conjugate | Free Anti-HIV | | |
| 0 | 100 | 100 | 0 | 0 |
| 5 | 95 | 58 | 3 | 7 |
| 10 | 91 | 40 | 5 | 19 |
| 15 | 84 | 33 | 7 | 26 |
| 20 | 79 | 27 | 9 | 30 |
| 30 | 75 | 20 | 10 | 35 |

EXAMPLE 13

Cationic Block Copolymer Synthesis 1,4-dibromobutane (5.4 g, 25 mmoles, from Aldrich Co., Milwaukee, Wis.) was added to a solution of N-(3-aminiopropyl)-1,3-propanediamine (6.55 g, 50 mmoles, from Aldrich Co.) dissolved in 100 ml of 1,4-dioxane. This reaction mixture was stirred at 20° C. for 16 h. The product of this reaction spontaneously precipitates from solution as the hydrobromide salt. This precipitated first intermediate was collected and twice dried by rota-evaporation from a solution of 10% triethylamine in methanol. This evaporation procedure was effective to remove substantial amounts of the bromide salt. The first intermediate was dissolved in 50 ml of 1,4-dioxane and reacted with 2.7 g (12.5 mmoles) of 1,4-dibromobutane. Again, the reaction proceeded for 16 h at 20° C., and the resulting second intermediate was recovered and dried as above.

The second intermediate was neutralized with acetic acid to a pH of 7–8 and purified by gel filtration on Sephadex G-25, using an aqueous eluent. Three major polymine fractions were obtained, having apparent molecular weights of 1060, 700 and 500, respectively.

Poly(oxyethyleneglycol) (1.5 g, M.W. 1500, from Fluka) was dissolved in 8 ml of 1,4-dioxane and reacted with 0.17 g (1 mmole) of N,N'-carbonylimidazole (Aldrich Co.) at 20° C. for 3 h. The reaction mixture was divided into two parts. Each part was mixed with 4 ml of a 10% (w/v) solution of either the 1060 or 700 MW polyimine fraction, which solution further contained 0.01 N NaOH. The mixture was stirred for 16 h at 20° C. From this mixture, block copolymers of formula (XX) and various MW ranges were isolated by gel filtration.

EXAMPLE 14

Cationic Block Copolymer Synthesis 0.5 g of a succinimidyl carbonate of methoxy-PEG (MW 5000, Shearwater Polymers, Inc., USA) was dissolved in 1,4-dioxane. This dioxane solution was added to an aqueous solution containing 0.2 g of the 1060 MW polyimine polymer described above, which aqueous solution further included 0.01 N NaOH. This reaction mixture was stirred at 20° C. for 16 h. A polymer of formula (XXII) was isolated from the reaction by gel filtration.

EXAMPLE 15

Cationic Block Copolymer Synthesis 1.5 g of poly(oxyethyleneglylol) (MW 8000, Fluka) were dissolved in 8 ml of 1,4-dioxane. 0.34 g (2 mmole) of N,N'-carbonylimidazole (Aldrich Co.) were added to the solution and reacted for 3 h at 20° C. 8 ml of an aqueous solution containing 0.01 N NaOH and 15% (w/v) of the 500 MW polyimine polymer described above in Example 13 was then added to the first reaction mixture. The resulting mixture was reacted for 16 h at 20° C. with stirring. A polymer of formula (XXIII) was isolated from the second reaction mixture by gel filtration.

EXAMPLE 16

Conjugate Synthesis with Oligonucleotide

A 12-mer oligonucleotide, 5'-CGTTCCTCCTGU ("Oligo A") complimentary to the splicing site (positions 983–994 on the viral genome) of the early mRNA of type 1 Herpes Simplex Virus ("HSV-1"), was synthesized using a 380B-02 DNA-synthesizer (Applied Biosystems, CA). The synthesizer used phosporamidite chemistry and an 8 min. synthesis cycle. Cycle conditions and preparation of the crude product were done as recommended by Applied Biosystems. The crude Oligo A obtained from the synthesis was precipitated from a 1 M LiCl solution (0.5 ml) with acetone (2 ml). The precipitate was dissolved in triethylammonium acetate buffer and purified by reverse-phase high performance liquid chromatography on a Silasorb C18 column (9×250 mm, Gilson, France) developed with an acetonitrile gradient in a 20 mM TEAA buffer (pH 8.5).

The 3'-terminal of the purified Oligo A was oxidized with periodate to create an aldehyde and conjugated by reductive alkylation with a hexamethylene-diamine linker, creating an amine derivative. See Che-Chung et al., *Biochem. Internat.,* 25:767 (1991); Vinogradov et al., *BBRC,* 203:959 (1994). "Pluronic A", a block copolymer of formula (XIV)(x=25, y=38, z=25) was similarly oxidized to create terminal aldehydes. The amine derivative (1 mg) was dissolved in 100 μl of 0.1 M borate buffer (pH 9.0) and mixed with 2 mg of the Pluronic A derivative. 1.5 mg of sodium cyanoborohydride was added to the mixture to reduce the Schiffs bases formed between the amine and aldehyde groups. This reaction was allowed to proceed for 12 hours at 4° C. The polymeric product of this reaction was isolated by gel filtration chromatography on Sephadex LH-20, utilizing 90% aqueous isopropanol as the eluent. The conjugate so obtained is referred to hereinafter as "Oligo A Conjugate."

EXAMPLE 17

The Effect of Oligo A Conjugate on Virus Production

Oligo A and Oligo A Conjugate were separately dissolved in RPMI 1640 medium (ICN Biomedicals Inc., Costa Mesa, Calif.) to a final concentration of 0.2 mM (based on oligonucleotide absorbance). These stock solutions were then filtered through 0.22 μm filters to remove any possible bacterial or fungal contamination.

Monolayers of Vero cells were incubated for 1 hour at 37° C. in serum-free RPMI 1640 together with various concentrations of Oligo A or Oligo A Conjugate. The monolayers, while still exposed to oligonucleotides, were then infected with 1 plaque forming unit per cultured cell of HSV-1, strain L2 (from the Museum of Virus Strains of the D.I. Ivanovskii Institute of Virology, Russian Academy of Sciences, Russian Federation). This infection method has been described by Vinogradov et al., *BBRC,* 203:959 (1994). After 8 hours of exposure to virus and oligonucleotides, the medium on the cells was replaced with fresh medium containing 10% FCS. Medium from the cells was collected at 22 and 39 hours after the ineffective incubation, and the virus titer in the collected medium was determined as described in *Virology, A Practical Approach,* Mahy, Ed., IRL Press, Oxford Univ. Press, Washington, D.C. (1985). The results were as follows:

| Sample | | Infectious Titer of HSV-1 (PFU/ml) | |
|---|---|---|---|
| concentration (mM) | Oligonucleotide concentration (μM) | 22 hours past infection | 39 hours past infection |
| Control (cells without oligonucleotides) | 0 | $5 \times 10^6$ | $1 \times 10^7$ |
| Oligo A | 10 | $3 \times 10^6$ | $5 \times 10^6$ |
|  | 5 | $5 \times 10^6$ | $1 \times 10^7$ |
|  | 2 | $5 \times 10^6$ | $1 \times 10^7$ |
|  | 1 | $5 \times 10^6$ | $1 \times 10^7$ |
| Oligo A | 10 | 0 | 0 |

-continued

| Sample | | Infectious Titer of HSV-1 (PFU/ml) | |
|---|---|---|---|
| concentration (mM) | Oligonucleotide concentration (μM) | 22 hours past infection | 39 hours past infection |
| Conjugate | 5 | 0 | $5 \times 10^2$ |
|  | 2 | $1 \times 10^3$ | $7 \times 10^3$ |
|  | 1 | $5 \times 10^4$ | $3 \times 10^6$ |

EXAMPLE 18

Synthesis of a Phosphonate Monomer 40 mmoles of butanediol-1,3 (Merck) dissolved in 50 ml of anhydrous pyridine (Aldrich) were reacted with 20 mmoles 4,4'-dimethoxytritylchloride (Sigma) for 1.5 hours at 20° C. The reaction was monitored using thin layer chromatography on the silicagel plates (Merck) developed with a chloroform:methanol (95:5). The Rf of the product was 0.6. The reaction mixture was added to 200 ml of an 8% aqueous solution of the sodium bicarbonate and the product extracted with chloroform. The chloroform extract was evaporated in vacuum and the resulting oily first intermediate was used in the next stage of the synthesis.

12 mmoles of first intermediate were dissolved in 30 ml of ahydrous 1,4-dioxane, containing 3.14 ml (18 mmoles) of diisopropylethylamine (Aldrich). 18 mmoles of salicylchlorophosphite (Sigma) dissolved in 10 ml of ahydrous 1,4-dioxane were added to the diisopropyethylamine solution in small portions under an inert, argon atmosphere. The reaction mixture was incubated during 1 hour at 20° C. The reaction was monitored by the thin layer chromatography as described above. The Rf of the product was 0.05. 10 mls of water were added to the reaction mixture. After 30 min., the solvent was evaporated. The product was dissolved in 100 ml of chloroform and the solution obtained was washed stepwise with (1) 100 ml of 8% aqueous solution of the sodium bicarbonate, (2) 100 ml of 0.2 M triethyammoniumacelate solution (pH 7.2), and (3) 100 ml of water. The organic solvent was evaporated and the oily remainder, containing the phosphonate monomer was purified by chromatography on silicagel column, using stepwise gradient of (1) chloroform, (2) 3% methanol in chloroform and (3) 6% methanol in chloroform. The yield of the monomer was 4.1 g (=7.3 mmol, 63%). The product, having structure:

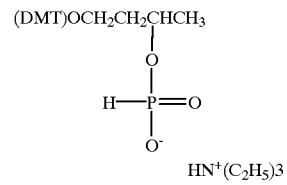

wherein DMT represents a dimethoxytrityl group, can be termed "Phosphonate Monomer A."

EXAMPLE 19

Synthesis of Polycation BDP

A 0.05 M solution of the phosphonate Monomer A in anhydrous pyridine:acetonitrile mixture (1:1) was placed in the position 6 of the DNA-synthesator (model 380-B02, Applied Biosystems, CA). A 2% solution of adamantoilchloride (Sigma) in the mixture acetonitrile:pyridine (95:5) was used as a condensing agent. The synthesis was conducted using the program modified for an H-phosphonate cycle (Sinha and Striepeke, *Oligonucleotides and Analogues: A Practical Approach,* Eckstein Ed. IRL Press, Oxford, p.185 (1991)) and the DMT-group was preserved after the synthesis was complete. Adenosine (4 µmoles) immobilized on a standard CPG-500 solid support was used as a first unit during the polymer synthesis (Vinogradov et al. *BBRC,* 203, 959 (1994). The synthesizer was programmed to add Phosphonate Monomer A repeating units to the adenosine monomer. Following all synthesis steps, the H-phosphonate groups on the immobilized substrate were oxidized with the solution of 104 mg of hexamethylenediamine (Sigma) in 0.6 ml of a mixture of anhydrous pyridine:$CCl_4$ (5:1) applied for 15 min. at 20° C., then the carrier was washed with the pyridine:acetonitrile mixture (1:1).

Deblocking and cap removal was achieved by ammonolysis (*Oligonucleotides and Analogues: A Practical Approach,* Eckstein Ed. IRL Press, Oxford, 1991). The product was purified by HPLC using Silasorb C., column (9×250 mm. Gilson, France) in the acetonitrile gradient (0–80%). The peak, containing dimethoxytritylated-product was collected, the solvent was evaporated and the remainder was treated with 80% acetic acid (20 min). The acetic acid was evaporated and the polycation was purified again by HPLC. The yield of the 15-mer (counted in terms of Phosphonate Monomer A) is 50% (2.2 µmoles). This created a polymer according to formula A. The polymer will be termed hereinafter "BDP."

EXAMPLE 20

Solid Phase Synthesis of the Diblock Copolymer Polyoxyethylene-BDP

Dimethoxytrityl-polyethyleneoxide-H-phosphonate was synthesized as described in Example 18 using polyethyleneglycol (1500 M.W. from Fluka) instead of butanediol-1, 3. The BDP polycation was synthesized as described in Example 19, except that, at the last stage of the chain growth, dimethoxytrityl-polyethyleneoxide-H-phosphonate was introduced as the last building block. The H-phosphonate groups of the block copolymer were oxidized as described in Example 19 using tetramethylenediamine (Sigma) instead of hexamethylenadiamine, resulting in the formation of phosphonamide bonds between the diamines and the backbone phosphates.

EXAMPLE 21

Solid Phase Synthesis of the Oligonucleotide-BDP Diblock Copolymer

A diblock copolymer comprising 12-mer oligonucleotide, 5'-GGTTCCTCCTGU (Oligo A, complementary to the splicing site of the early mRNA of type 1 Herpes Simplex Virus (HSV-1), Vinogradov et al., *BBRC,* 203:959 (1994)) and the BDP polymer was synthesized in DNA synthesator. First the BDP polymer was synthesized as described in Example 19, except that it was not removed from the support. Then the oligonucleotide chain was synthesized step-wise onto BDP polycationic polymer linked to the solid state support using the standard phosphoroamidite chemistry as described by Vinogradov et al. *BBRC,* 203, 959 (1994). The H-phosphonate groups of the diblock copolymer were oxidized as described in Example 19 using tetamethylenediamine (Sigma) instead of hexamethylenediamine.

EXAMPLE 22

Effect of Oligonucleotide-BDP Diblock Copolymer on Viral Growth

The experiment was performed exactly as described in Example 17 except that (1) the oligonucleotide-BDP copolymer of Example 21 was used and (2) a single concentration of oligonucleotide-BDP copolymer (conjugate) was used (4,4M).

| Sample | Virus titre after 39 hours |
| --- | --- |
| Control (without oligonucleotide) | $500 \times 10^4$ |
| Nonmodified Oligo A | $500 \times 10^4$ |
| Diblock | $5 \times 10^4$ |

EXAMPLE 23

Synthesis of Branched Polyimine Polycation

A. The polyimine polycation ("polyspermine") was obtained by stepwise polycondensation of N-(3-aminopropyl)-1,3-propanediamine and 1,4-dibromobutane as described in Example 13 and used without conjugating to poly(ethylene glycol).

B. The polyimine polycation synthesized in A was modified by dansyl chloride to obtain a fluorescent dansyl-labeled substance, purified by thin layer chromatography and a major component of the mixture (over 75% in most batches) was analyzed by electrospray massspectrometry in positive charge mode. The results were compared with mass-spectra obtained for the N-(3-aminopropyl)-1,3-propanediamine modified with dansyl chloride. Dansyl-labeled N-(3-aminopropyl)-1,3-propanediamine gave a four-modal peak at M+1, M+2, M+3, and M+4 (667.6, 668.5, 669.6, and 670.5). In the spectrum of the polycondensation products there were observed two types of polymodal peaks: M and M+54. For M-peaks two distinct groups were observed, with M/2H+ and M/H+, equal to 598.5 and 1195.6 respectively. This molecular mass was very close to a linear polycation with 12 nitrogen atoms (1221). M+54 peaks at 1249.8 and 652.5 correspond to a polycation with $CH_2CH_2CH_2CH_2$ cross-links.

C. 1H-NMR spectra were obtained for the samples of the polyimine polycation synthesized in A and dissolved in DMSO. Three groups of signals were observed at 1.40–1.80 ppm (Ha), 1.80–2.20 ppm (Hb), and 2.35–2.80 ppm (Hc). Ha related to $CH_2CH_2CH_2CH_2$ protons, Hb related to $CH_2CH_2CH_2$ protons, Hc related to —$NHCH_2$ and protons. Integration of resonance signals for these three groups gave a ratio Ha:Hb:Hc equal to 1.00:0.75:1.20. The theoretical ratio for linear polycations with 12 nitrogen atoms is 1.00:1.33:3.67. Increase in Hb:Ha and Hc:Ha ratios suggested presence of branched structures with a mixture of primary, secondary and tertiary amines.

D. The concentration of primary amino groups in the polyimine polycation synthesized in A was determined by fluorescamine method as described by Weigele et al., *J. Amer. Chem. Soc.,* 94:5927 (1972). The total amount of primary, secondary, and tertiary amino groups in the polycondensation product was determined using potentiometric titration. The ratio of the total amount of primary, secondary, and tertiary amino groups to the amount primary amino groups equals 2.7. Given the molecular masses of the condensation product determined using mass-spectrometry the result of this experiment suggests considerable branching, i.e. the presence of tertiary amines.

EXAMPLE 24

Synthesis of Linear Polyimine Polycation

Linear polycations of polyimine type are synthesized by condensation of a diaminoalkyl and bis-aldehyde in the presence of sodium cyanoborohydride using a modified reductive amination procedure described by Aziz et al., *J. Pharmac. Exper. Therapeutics,* 274:181 (1995). 0.33 g of malonaldehyde bis(dimethyl acetal) was added in 10 ml of 0.5 N HCl and stirred for 1 hour at 20° C. to obtain free bis-aldehyde. 1.27 g of N,N'-bis[3-aminopropyl]-1,4-butanediamine was added to this solution and pH was adjusted to 5.0. The mixture was allowed to stay for 1 h at 37° C., then 1.27 g of N,N'-bis[3-aminopropyl]-1,4-butanediamine was added to it and pH was adjusted to 7.0 using sodium carbonate solution. The reaction mixture was treated with 0.26 g of sodium cyanoborohydride and left for additional 1 h at 37° C. The final slightly yellow solution was desalted by gel permeation chromatography on the Sephadex G-25 column in 10% methanol and first high-molecular weight fractions revealing primary aminogroups in ninhydrine test were freeze-dried. This yielded 0.43 g of the following polyimine polycation:

EXAMPLE 25

Synthesis of Cationic Block Copolymer 1.5 g of poly(ethylene glycol), methyl ester, mw. 5000 Mw. (Sigma) was activated by 0.25 g of 1,1'-carbonyldiimidazole in 10 ml of anhydrous acetonitrile for 3 hrs at room temperature. The solvent was evaporated in vacuo, the residue redissolved in water and dialyzed through Membra-Cel MD-25-03.5 membrane with cutoff 3500 Da against water. Desalted solution was concentrated in vacuo and used in a reaction with 2-fold excess of poly-L-lysine, Mw. 4000, in methanol-water solution for 16–24 hrs at room temperature. The conjugate obtained was purified by gel-permeation column chromatography on Sephadex-50 (fine) (Pharmacia) in water and then by reverse phase chromatography on semi-preparative column (Vydac C18 5u , 10 mm×25 cm) in acetonitrile concentration gradient. The yield was 70%. Content of aminogroups was measured by fluorescamine method and total nitrogen content was determined by elemental analysis to assess the purity of the conjugates. Usually it was about 75–90% based on graviometry.

EXAMPLE 26

Synthesis of Cationic Block Copolymer

Following the procedure of Example 25 but substituting the 2-fold excess of poly-L-lysine by the same excess of polyethyleneimine, $(NHCH_2CH_2)_x[N(CH_2CH_2)CH_2CH_2]_y$, Mw. 2000 (Aldrich Co.), 0.4 g of the following cationic diblock copolymer is obtained:

EXAMPLE 27

Synthesis of Grafted Copolymer

A. 24 g (3 mmol) of poly(ethylene glycol), mw 8000 (Aldrich Co.) were dried by co-evaporation with anhydrous pyridine in vacuo and dissolved in 50 ml of anhydrous acetonitrile. Then 0.51 g (1.5 mmol) of 4,4'-dimethoxytrityl chloride in 30 ml of anhydrous pyridine was added to this solution dropwise under continuous stirring during 30 min. The mixture was allowed to stand for additional 2 h at room temperature, then the solvents were evaporated in vacuo. The residue was dissolved in 50 ml of dichloromethane, extracted with 5% sodium bicarbonate (2×30 ml), and applied on the Silicagel column (3×45 cm, 40–60 μm). Stepwise elution with dichloromethane-methanol solutions separated a slightly yellow mono-4,4'-dimethoxytrityl-derivative of poly(ethylene glycol) with an yield about 75–85%. The side product of the reaction (10–15% yield) was the bis-4,4'-dimethoxytrityl-derivative of poly(ethylene glycol).

B. 1.5 g of mono-4,4'-dimethoxytrityl-derivative of poly (ethylene glycol) obtained in A was activated by 0.25 g of 1,1'-carbonyldiimidazole in 10 ml of anhydrous acetonitrile for 3 hrs at room temperature. The solvent was evaporated in vacuo, the residue redissolved in water and dialyzed through Membra-Cel MD-25-03.5 membrane with cutoff 3500 Da against water. Desalted solution was concentrated in vacuo and then reacted with poly-L-lysine, Mw. 19000 in methanol-water solution for 24 h at room temperature at a molar ratio of poly(ethylene glycol) to free aminogroups of poly-L-lysine 0.7:1.0. The conjugate obtained was purified by gel-permeation column chromatography on Sephadex-50 (fine) (Pharmacia) in water and then by reverse phase chromatography on semi-preparative column (Vydac C18 5u, 10 mm×25 cm) in acetonitrile concentration gradient. This yields a grafted polylysine copolymer at 35% yield in which 50% of free aminogroups are substituted with poly (ethylene glycol) as determined by fluorescamine method.

EXAMPLE 28

Synthesis of Grafted Copolymer

A. 24 g (3 mmol) of poly(ethylene glycol), mw 8000 (Aldrich Co.) were dried by co-evaporation with anhydrous pyridine in vacuo and dissolved in 50 ml of anhydrous acetonitrile. Then 0.51 g (1.5 mmol) of 4,4'-dimethoxytrityl chloride in 30 ml of anhydrous pyridine was added to this solution dropwise under continuous stirring during 30 min. The mixture was allowed to stand for additional 2 h at room temperature, then the solvents were evaporated in vacuo. The residue was dissolved in 50 ml of dichloromethane, extracted with 5% sodium bicarbonate (2×30 ml), and applied on the Silicagel column (3×45 cm, 40–60 μm). Stepwise elution with dichloromethane-methanol solutions separated a slightly yellow mono-4,4'-dimethoxytrityl-derivative of poly(ethylene glycol) with an yield about 75–85%. The side product of the reaction (10–15% yield) was the bis-4,4'-dimethoxytrityl-derivative of poly(ethylene glycol).

B. 1.5 g of mono-4,4'-dimethoxytrityl-derivative of poly (ethylene glycol) obtained in A was activated by 0.25 g of 1,1'-carbonyldiimidazole in 10 ml of anhydrous acetonitrile for 3 hrs at room temperature. The solvent was evaporated in vacuo, the residue redissolved in water and dialyzed through Membra-Cel MD-25-03.5 membrane with cutoff 3500 Da against water. Desalted solution was concentrated in vacuo and then reacted with polyethyleneimine, Mw. 25,000 in methanol-water solution for 24 h at room temperature at a molar ratio of poly(ethylene glycol) to free aminogroups of polyethyleneimine 0.7:1.0. The conjugate obtained was purified by gel-permeation column chromatography on Sephadex-50 (fine) (Pharmacia) in water and then by reverse phase chromatography on semi-preparative column (Vydac C185 μm, 10 mm×25 cm) in acetonitrile concentration gradient. This yields a grafted polyethyleneimine block copolymer at 85% in which 45% of free aminogroups are substituted with poly(ethylene glycol) as determined by fluorescamine method as described by Weigele et al. (*J. Amer. Chem. Soc.*, 1972, 94:5927).

EXAMPLE 29

Synthesis of Grafted Copolymer

Following the procedure of Example 28 but using a molar ratio of activated poly(ethylene glycol) to free aminogroups of polyethyleneimine 0.3:1.0, there is obtained in 80% yield a grafted polyethyleneimine copolymer in which 24% of free aminogroups are substituted with poly(ethylene glycol).

EXAMPLE 30

Synthesis of Cationic Block Copolymer

Following the procedure of Example 26 but substituting 6.0 g of polyethyleneglycol, mw 20,000 for the excess of polyethylene glycol, mw 5,000 there is obtained 6.0 g of the cationic block copolymer:

EXAMPLE 31

Synthesis of Cationic Block Copolymer

A. Following the procedure of Example 26 but substituting 1.5 g of polyethyleneglycol, Mw. 5,000 by 2.4 g of polyethyleneglycol, Mw. 5,000 (Aldrich Co.) there is obtained 1.2 g of the cationic block copolymer containing polyethyleneinmine and polyethyleneglycol chain segments.

B. The molecular mass of this block-copolymer was determined by static light scattering method using DAWN multi-angle laser photometer (Wyatt Technology, Santa Barbara, Calif.) which operated at 15 angles and equipped with He-Ne laser (632.8 nm). The samples of the block copolymer were dialyzed through membrane with cutoff 3,500 Da against $4.5 \times 10^{-3}$ g/ml NaCl and then filtered directly into flow cell used for light scattering experiments. Weigh-average molecular mass was calculated on the base of four measurements. Cell constant was determined by calibration with different concentrations of NaCl. Specific refractive index increment (dn/dc) was measured using Wyatt/Optilab 903 interferometric refractometer at 632.8 nm. The molecular mass of the sample obtained was 16,000, suggesting that this polymer contained approximately one polyethyleneinmine segment and two polyethyleneglycol segments.

C. The number of the primary aminogroups in the synthesized sample of the copolymer was determined using a modified procedure described by Weigele et al. (*J. Amer. Chem. Soc.*, 1972, 94:5927). To 1.5 ml of a sample in 20 mM sodium borate, pH 9.5 (aminogroups concentration up to 100 μM) 0.25 ml of fluorescamine solution (0.024%, Sigma) in acetone was added and vortexed for 5 min. The measurements have been made on spectrofluorometer Shimadzu at excitation wavelength 384 nm and at 430 to 510 nm emission wavelength range. Extinction coefficient at emission 475 nm was determined as equal to $1.58 \times 10^6$ M$^-$. The specific amount of primary aminogroups was 0.69 mmol/g.

EXAMPLE 32

Synthesis of Grafted Copolymer

Following the procedure of Example 28 but substituting 24 g of poly(ethylene glycol) by the same amount of Pluronic L61 (BASF Co.) and using a molar ratio of activated Pluronic L61 to free aminogroups of polyethyleneimine 0.3:1.0, there is obtained in 22% yield a grafted polyethyleneimine copolymer in which 8% of free aminogroups are substituted with Pluronic L61.

EXAMPLE 33

Synthesis of Grafted Copolymer

Following the procedure of Example 28 but substituting 24 g of poly(ethylene glycol), by the same amount of Pluronic P85 and using a molar ratio of activated Pluronic P85 to free aminogroups of polyethyleneimine 0.3:1.0 there is obtained in 70% yield a grafted polyethyleneimine copolymer in which 11% of free aminogroups of polyethyleneimine are substituted with Pluronic P85.

EXAMPLE 34

Synthesis of Grafted Copolymer

Following the procedure of Example 28 but substituting 24 g of poly(ethylene glycol), by the same amount of Pluronic P123 (BASF Co.) and using a molar ratio of activated Pluronic P123 to free aminogroups of polyethyleneimine 0.3:1.0 there is obtained in 30% yield a grafted polylysine copolymer in which 9% of free aminogroups are substituted with Pluronic P123.

EXAMPLE 35

Synthesis of Grafted Copolymer

Following the procedure of Example 28 but substituting 24 g of poly(ethylene glycol), by the same amount of Pluronic F38 (BASF Co.) and using a molar ratio of activated Pluronic F38 to free aminogroups of polyethyleneimine 0.3:1.0 there is obtained in 40% yield a grafted polylysine copolymer in which 9% of free aminogroups are substituted with Pluronic F38.

EXAMPLE 36

Synthesis of Multi-Grafted Copolymer

Following the procedure of Example 28 but substituting polyethyleneimine by polyethyleneimine modified with Pluronic L123 (BASF Co.) obtained in Example 35 and using a molar ratio of activated poly(ethylene glycol) to free aminogroups of modified polyethyleneimine 0.4:1.0 there is obtained in 20% yield a grafted polyethyleneimine copolymer in which 9% of free aminogroups are substituted with Pluronic L123 and 30% of groups are substituted with poly(ethylene glycol).

EXAMPLE 37

Complex with Oligonucleotide

A. Model phosphorothioate oligodeoxyribonucleotide PS-dT20 was synthesized using ABI 291 DNA Synthesizer (Applied Biosystems, San Diego, Calif.) following the standard protocols. After ammonia deprotection the oligonucleotide was twice precipitated by ethanol and then used without purification.

B. The complex formed between the PS-dT20 and polyethyleneimine-poly(ethylene glycol) block copolymer obtained in Example 28 was obtained by mixing the aqueous solutions of these polymers in 10 mM phosphate buffer, pH 7.4 so that the ratio of the primary amino groups of the block copolymer to the phosphate charges of the PS-dT20 was 1.0. All solutions were prepared using double distilled water and were filtered repeatedly through the Millipore membrane with pore size 0.22 μM.

C. The electrophoretic mobility (EPM) and the size of the particles of the complex synthesized in B were determine. The EPM measurements were performed at 25° C. with an electrical field strength of 15–18 V/cm using "ZetaPlus" Zeta Potential Analyzer (Brookhaven Instrument Co.) with 15 mV solid state laser operated at a laser wavelength of 635 nm. The zeta-potential of the particles was calculated from the EPM values using the Smoluchowski equation. Effective hydrodynamic diameter was measured by photon correlation spectroscopy using the same instrument equipped with the Multi Angle Option. The sizing measurements were performed at 25° C. at an angle of 90°. The zeta potential of this sample was close to zero, suggesting that particles were electroneutral. The average diameter of the particles was 35 nm.

EXAMPLE 38

Stability Against Nuclease Digestion

100 μg of the complex formed between the PS-dT20 and polyethyleneimine-poly(ethylene glycol) block copolymer obtained in Example 39 was treated by 1 mg of snake venom phosphodiesterase (Phosphodiesterase I from *Crotalis adamanteus*, 0.024 units/mg, Sigma) for 2 and 18 hrs at 37° C. Reaction mixtures were analyzed by gel permeation HPLC for digested PS-dT20. The digestion of the PS-dT20 in this complex was less than 5%. In contrast, free PS-dT20 treated with the same concentration of enzyme for the same time interval was digested completely.

EXAMPLE 39

Accumulation of Oligonucleotide in Caco-2 Monolayers

A. A 5'-aminohexyl PS-dT20 oligonucleotide was synthesized using ABI 291 DNA Synthesizer (Applied Biosystems, San Diego, Calif.) following the standard protocols. After ammonia deprotection the oligonucleotide was twice precipitated by ethanol and then used without purification. 5'-Aminohexyl PS-dT20 was labeled by reaction with fluorescein isothiocyanate (Sigma) following the manufacturer protocol. Fluorescein-labeled PS-ODN was separated from unreacted fluorophore using a Pharmacia PD-10 size exclusion.

B. The complex formed between the fluorescein-labeled PS-dT20 and polyethyleneiminepoly(ethylene glycol) block copolymer was synthesized as described in Example 37 but using fluorescein-labeled PS-dT20 instead of PS-dT20.

C. Caco-2 cells, originating from a human colorectal carcinoma (Fogh et al. J. Natl. Cancer Inst., 59:221-226, 1977) were kindly provided by Borchardt R. T. (The University of Kansas, Lawrence, Kans.). The cells were maintained in Dulbecco's Modified Eagle's Medium (DMEM), containing 10% heat-inactivated fetal bovine serum (FBS), 1% non-essential amino acids, benzylpenicilin (100 μ/ml) and streptomycin (10 μg/ml), in an atmosphere of 90% air and 10% $CO_2$ as described by Artursson (*J. Pharm. Sci.*, 79:476–482, 1990). All tissue culture media were obtained from Gibco Life Technologies, Inc. (Grand Island, N.Y.). The cells were grown on collagen coated polycarbonate filter chamber inserts (Transwell, Costar Brand Tissue Culture Products, Contd.; pore size 0.4 μm; diameter 24.5 mm). 250,000 cells were added to each insert and cells of passage number 32–45 were used. The cells were fed every second day and were allowed to grow and differentiate for up to 14 days before the monolayers were used in the following absorbtion experiments.

D. Caco-2 cell monolayers were preincubated for 30 min. at 37° C. with assay buffer, containing sodium chloride (122 mM), sodium bicarbonate (25 mM), glucose (10 mM), HEPES (10 mM), potassium chloride (3 mM), magnesium sulfate (1.2 mM), calcium chloride (1.4 mM) and potassium phosphate dibasic (0.4 mM). After this, the assay buffer was removed and the cells were exposed to 50 μM fluorescein-labeled PS-ODN or its complex in the assay buffer for 90 min. at 37° C. After that the dye solutions were removed and cell monolayers were washed three times with ice-cold PBS. Cells were then solubilized in 1.0% Triton X-100 and aliquots (25 μl) were removed for determination of cellular fluorescence using a Shimadzu RF5000 spectrofluorometer at λex=488 nm, λem=520 nm. Samples were also taken for protein determination using the Pierce BCA method. The amounts of fluorescein-labeled PS-dT20 absorbed by the cells was as follows:

| Sample | Cellular accumulation of oligonucleotide, nmol/mg protein |
| --- | --- |
| Free fluorescein-labeled PS-dT20 | 0.14 ± 0.03 |
| The complex | 0.5 ± 0.01 |

This demonstrates that incorporation of polynucleotide in the complex with the block copolymer increases cellular accumulation of polynucleotide by more than 3-times.

EXAMPLE 40

Transport of Oligonucleotide Across Caco-2 Monolayers

A. The filter-grown Caco-2 monolayers were used for oligonucleotide permeability studies after complete maturation, i.e., as from day 14 after plating. Filters were gently detached from the wells and placed in Side-Bi-Side diffusion cells from Crown Bio. Scientific, Inc. (Somerville, N.J.) maintained at 37° C.±0.1° C. This system is used as an in vitro model of human intestinal epithelium to evaluate oral bioavailability of drugs (Pauletti et al., *Pharm. Res.*, 14:11–17 (1977). Cell monolayers were preincubated for 30 minutes at 37° C. with the assay buffer, containing 10% heat-inactivated fetal bovine serum (FBS), 1% non-essential amino acids, benzylpenicilin (100 μ/ml) and streptomycin (10 μg/ml), added to both donor and receptor chambers (3 ml). After preincubation, the assay buffer in the receptor container was replaced by the fresh one, while the assay buffer in the donor container was replaced by 50 μM fluorescein-labeled PS-ODN or its complex in the assay buffer. To account for the integrity of the monolayers the R123 solutions in the donor container also contained $H^3$-labeled manitol, a paracellular marker (Dawson, J. Membrane Biol., 77:213–233 (1977) obtained from DuPont Corp. (Boston, Mass.). At 120 min., the solutions in the receptor chamber were removed for determination of fluorescein-labeled PS-ODN using a Shimadzu RF5000 fluorescent spectrophotometer (λex=488 nm, λem=520 nm) and H$^3$-manitol determination using a liquid scintillation counter (Hewlett Packard Instruments). Immediately after collecting the solutions in the receptor chamber 3 ml of fresh assay buffer was added to this chamber. The transport of fluorescein-labeled PS-ODN (or manitol) across Caco-2 cell monolayers was expressed as a percentage of the total fluorescein-labeled PS-ODN (or manitol) accumulated in the receptor chamber to the initial amounts of fluorescein-labeled PS-ODN (or manitol) in the donor chamber. A minimum of three different membranes was studied for each drug composition at multiple time points for each membrane. The results were as follows:

| Sample | PS-dT20 transport, % | Manitol transport, % |
|---|---|---|
| Free fluorescein-labeled PS-dT20 | 0.001 ± 0.0005 | 4.0 ± 0.1 |
| The complex | 0.075 ± 0.005 | 4.2 ± 0.02 |

This demonstrates that incorporation of polynucleotide in the complex with the block copolymer increases transport of this polynucleotide across Caco-2 monolayers by more than 7-times while the transport of paracellular marker is not affected.

EXAMPLE 41

In vitro Transfection of Plasmid DNA with Various Block Copolymers-based Formulations These experiments are performed in Cos-7 cells and carried out as follows; Cos-7 cells are used and are seeded at 7×10$^5$ per well in 12-well plate (Costar) and allowed to rest 24 hours before transfection (confluenly at 70%). Three μg of pGL3-Luc SV40 is formulated with the different polymers at various N/P ratios. The transfection mixture is prepared as follows; to an eppendorf tube containing 100 μl of DMEM supplemented with 1% Hepes the following is added; 30 μl of DNA at 0.1 mg/ml, 35 μl of polymer to be tested at various concentrations to get a variety of N/P ratios. The transfection mixture is allowed to incubate 5 minutes before completing to 1 ml with complete DMEM (10% FBS, 1% Hepes, 1% penicillin-streptomycin). Five hundred μl of the transfection mixture is added per well. Following a 4-hours transfection at 37° C. and under a 5% CO$_2$ atmosphere, the cells are rinsed with PBS and allowed to rest overnight in 1 ml of complete DMEM before being harvested to perform the luciferase assay according to Promega Corporation's recommendation. Briefly, the cells are lysed on ice for 30 minutes and then centrifuged at 13 000 g for 2 minutes. The supernatents are kept and analyzed for luciferase activity. The assay is performed as follows: 20 μl of supernatent is added to luminometric tubes containing 100 μl of luciferase substrate. Light emission is measured with a luminometer (Berthold) for a period of 5 seconds. The data is reported in relative light units per second and normalized for proteins with the BiCinchoninic Acid assay kit (Sigma). The results show that pluronic P123 conjugated to PEI improves transfection of CMV-Luc compared to PEI alone suggesting that the block copolymer moiety is advantageous for a better transfection. Note that P123 alone does not transfect cells and is totally inefficient like CMV-Luc alone. This observation is in contrast to the data shown in example 44 where P123 is used to improve gene expression in muscle.

| Transfection mixture | Luciferase signal (RLU/s/ug proteins) |
|---|---|
| CMV-Luc alone | 15 ± 4 |
| CMV-Luc + P123-PEI/123 | 1789456 ± 45789 |
| CMV-Luc + P123 | 26 ± 6 |
| CMV-Luc + PEI | 678543 ± 32591 |

EXAMPLE 42

Block Copolymers as Biological-modifiers of DNA Biodistribution

CMV-Luc (50 μg) or oligonucleotides (100 μg) are resuspended in a volume of 200 ul containing various block copolymers-based formulations and injected i.v. into C57B1/6 (6–8 week-old) female mice. Twenty-four hours following the injection the mice are sacrificed to harvest various organs in which luciferase activity is measured or in which oligonucleotide accumulation is determined. For plasmid DNA, all major organs are rapidly homogenized with a tissue grinder (Kontes Glass Co.) in cell lysis buffer (Promega Corporation) supplemented with protease inhibitors. The extraction mixture is kept on ice for 30 minutes and then centrifuged at a maximum speed for 2 minutes. The supernatents are kept and analyzed for luciferase activity. The assay is done as follows: 20 μl of supernatent is added to luminometric tubes containing 100 μl of luciferase substrate (Promega Corporation). Light emission is measured with a luminometer (Berthold) for a period of 5 seconds. The data is reported in pg of luciferase per mg of proteins. For oligonucleotides, the major organs are extracted twice with phenol:chloroform and precipitated with ethanol before quantification. The result show that with conventional liposomal formulation and PEI that gene expression is concentrated in the lungs which is a factor known to increase risks of pulmonary embolism. However, gene expression is redirected to liver when formulated with PEI conjugated to a hydrophobic block copolymer such as P123. In addition, when P123 is used alone, gene expression in various organs is very low except in muscle tissue. For oligonucleotides, the accumulation is observed is kidneys when a hydrophobic carrier (PEI conjugated to PEG) is used and is redirected to liver when a hydrophobic carrier (P85-PEI/P85) is used. Various and a multitude of mixture of block polymers can be prepared to give a wide range of hydrophobic and hydrophylic balances that can redirect gene expression and oligonucleotides accumulation in various regions of the body.

| Transfection mixture | Organs with the highest luciferase signal or with the highest accumulation of oligonucleotides |
|---|---|
| CMV-Luc alone | none |
| CMV-Luc + P123-PEI/P123 | Liver |
| CMV-Luc + P123 | Muscle |
| CMV-Luc + PEI | Lungs |
| CMV-Luc + Liposome (Dotap-chol) | Lungs |
| Oligo alone | Lungs and Liver |
| Oligo + PEI conjugated to PEG | Kidneys |
| Oligo + P85-PEI/P85 | Liver |

EXAMPLE 43

Intramuscular Transfection with Block Copolymers

In this experiment, block copolymers are used to improve gene expression in muscle (tibialis anterior) of C57B1/6

(6–7 week-old) female mice kept by groups of 4 and fed ad libidum. Five μg of CMV-driven plasmid DNA encoding for luciferase is formulated with block copolymers and injected i.m. into the tibialis anterior muscle. Before each intramuscular injection, the mice are anesthetized with a mixed solution of ketamine and xylazine. Mice are sacrificed 5 days following the i.m. injection and each injected muscle is dissected and rapidly homogenized with a tissue grinder (Kontes Glass Co.) in cell lysis buffer (Promega Corporation) supplemented with protease inhibitors. The extraction mixture is kept on ice for 30 minutes and then centrifuged at a maximum speed for 2 minutes. The supernatents are kept and analyzed for luciferase activity. The assay is done as follows: 20 μl of supernatent is added to luminometric tubes containing 100 μl of luciferase substrate (Promega Corporation). Light emission is measured with a luminometer (Berthold) for a period of 5 seconds. The data is reported in relative light units per second per tibialis anterior. As shown in the table below, block copolymers improve gene expression measured after 5 days post-injection. The use of a cationic reagent does not improve but inhibited gene expression. The reason of this improvement may lie in the block copolymer's property of changing the surface tension of muscle cells and thus increasing the uptake of plasmid DNA in myotubes.

| Treatment applied to tibialis anterior TA | Relative light units/second/TA | Fold-increase |
|---|---|---|
| Naked DNA (n = 26) | 31104 ± 1404 | — |
| Block copolymer formulated DNA (n = 18) | 205448 ± 17950 | 6.6 x |
| Cationic reagents n = 4 | 15 ± 3 | — |

EXAMPLE 44

Concentration of Block Popolymers Improving Gene Expression in Muscle

These experiments are carried out like in example 43 except that the concentration of block copolymers used for the i.m. injection is titrated. The concentrations of block copolymers used to perform intramuscular delivery of plasmid DNA are low. The concentrations of block copolymers used for intramuscular injection do not form gels. The solutions of block polymers consist in micelles and unimers of block polymers. The concentrations improving intramuscular gene expression are lower than 0.1% as shown below with the arrow. This concentration is about 100 times lower than the Maximal Tolerable Dose when the same block copolymers are injected I.V. Also, some combination of block copolymers can even improve further gene expression.

| PLURONIC P123 | |
|---|---|
| P123 (%) | RLU/s/T.A. muscle |
| 0 | 31005 ± 5619 |
| 0.0007 | 6052 ± 1778 |
| 0.007 | 100499 ± 30455 |
| 0.07 | => 130113 ± 46871 |
| 0.7 | 5368 ± 1505 |
| 7 | 160 ± 23 |

| COMBINATION OF PLURONIC F127/L61 | |
|---|---|
| F127/L61 (%) | RLU/s/T.A. muscle |
| 0 | 62565 ± 7569 |
| 0.01 | => 564397 ± 53813 |
| 0.05 | 500584 ± 40491 |
| 0.1 | 299050 ± 29592 |

EXAMPLE 45

Prolongation of Gene Expression with Block Copolymers

In this experiment, plasmid DNA encoding for luciferase is formulated with block copolymers like in example 43 except that the muscles are harvested after 48 hours and 2 weeks. As shown in the table below gene expression is prolonged with block copolymers.

| | After 48 hours (RLU/s/T.A. muscle) | After 2 weeks (RLU/s/T.A. muscle) |
|---|---|---|
| Naked DNA (n = 6) | 17143 ± 2886 | 1389 ± 405 |
| Block copolymer formulated DNA (n = 18) | 54377 ± 12486 | 20121 ± 7934 |

EXAMPLE 46

Kinetics of Gene Expression in Muscle with Block Copolymers

The kinetic experiments are prepared in conditions like that described in example 43 except that the muscles are harvested at day 1, 2, 3, 4, and 7. As shown in the table below gene expression starts earlier with block copolymers and remained the same over a period of 7 days.

| Day | Naked DNA (RLU/s/T.A. muscle) | DNA formulated with block copolymers (RLU/s/T.A. muscle) |
|---|---|---|
| 1 | 93419 ± 10835 | 526902 ± 39724 |
| 2 | 141705 ± 8293 | 722485 ± 43789 |
| 3 | 59663 ± 5558 | 311470 ± 20066 |
| 4 | 786200 ± 77419 | 1295196 ± 82725 |
| 7 | 168350 ± 11103 | 1202503 ± 108929 |

EXAMPLE 47

Cross-species Comparison of Intramuscular Gene Expression

Block copolymers are used to formulate plasmid DNA like in example 43 but injected to 2 different species, mice and rats. Tibialis anterior of 6–8 weeks old mice and 3 months old rats are harvested 48 hours following the intramuscular injection. Two assumptions can be drawn from the table shown below; (1) block copolymers can be applied to more than one species and likely to be applicable to other species like humans, and (2) block copolymers promote gene expression in older animal suggesting that block copolymers are likely to facilitate the transfection of mature myofibers.

|  | 6–8 week old mice (RLU/s/T.A. muscle) | 3 month old rats (RLU/s/T.A. muscle) |
| --- | --- | --- |
| Naked DNA | 17143 ± 2886 | 2749 ± 839 |
| Block copolymer-formulated DNA | 54377 ± 12486 | 70504 ± 8483 |

EXAMPLE 48

Treatment of Ischemic Tissues with Block Copolymers

Ten days after ischemia is induced in one rabbit hindlimb, 500 μg of phVEGF165 (or any other DNA plasmid encoding for growth factors known to promote formation of collateral blood vessels such as basic FGF) is formulated with 0.1% w/v of block copolymers is injected I.M. into the ischemic hindlimb muscles (Tsurumi Y. et al., *Circulation,* 94:12, 3281–90 (1996)). Thirty days later, an angiography is performed to recognize collateral vessels and histology analyses are carried out to identify capillaries. Ischemic skeletal muscle represents a promising target for gene therapy with naked plasmid DNA formulated with block copolymers. I.M. transfection of genes encoding angiogenic cytokines, particularly those that are naturally secreted by intact cells, may constitute an alternative treatment strategy for patients with extensive peripheral vascular disease.

EXAMPLE 49

Block Copolymers used for Gene-based Vaccination

Block copolymers could be used to raise any humoral and cellular immune response against various antigens associated with diseases (cancer, viral infection, etc.). The following example focuses but not limited to HIV. A block copolymer formulation containing a plasmid DNA construct consisting in gp120 gene of HIV, driven by a cytomegalovirus (CMV) promoter is prepared. A volume of 50 μl of a block copolymer formulation is prepared containing 5 μg of gp120 plasmid DNA and 0.01% of block copolymer is injected into the tibialis anterior muscle. At about 2 weeks after injection, the muscle is removed from the injection site, and prepared as a cell lysate according to the procedures of example 41 to detect the presence of gp120 by means of ELISA kits (Abbot Labs, Chicago, Ill.). The ability of gp120 antibody present in serum of the plasmid DNA vaccinated mice to protect against HIV infection is determined by a HT4-6C plaque reduction assay, as follows: HT4-6C cells (CD4$^+$ HeLa cells) are grown in culture in RPMI media (BRL, Gaithersburg, Md.). The group of cells is then divided into batches. Some of the batches are infected with HIV by adding approximately $10^5$ to $10^6$ infectious units of HIV to approximately $10^7$ HT4-6C cells. Other batches are tested for the protective effect of gp120 immune serum against HIV infection by adding both the HIV and approximately 50 μl of serum from a mouse vaccinated with gp120 plasmid DNA. After 3 days of incubation, the cells of all batches are washed, fixed and stained with crystal violet, and the number of plaques counted. The protective effect of gp120 immune serum is determined as the reduction in the number of plaques in the batches of cells treated with both gp120 plasmid DNA-vaccinated mouse serum and HIV compared to the number in batches treated with HIV alone.

EXAMPLE 50

Functional Expression of Dystrophin in Dystrophic Mouse Muscle in Vivo

A plasmid containing the dystrophin gene under control of the Rous Sarcoma virus promoter is prepared from the Xp21 plasmid containing the complete dystrophin coding region and the SV40 poly. 200 μg of the plasmid in 100 μl of Dystrophin abnormalities of Duchenne's/Becher Muscular 0.1% block copolymers solution is injected into the quadriceps the mutant mouse strain lacking the dystrophin gene product (MDX mouse; Jackson labs). Expression of functional dystrophin is monitored 7 days post injection by immunohistochemistry according to the procedures described by Watkins et al. and using the same anti-dystrophin antibody (anti-60 kd antibody with a fluorescent secondary antibody). Functional expression of the dystrophin gene product in the dystrophic mice is detected by comparing the pattern of fluorescence observed in cross-sections of quadriceps muscle from injected animals, with the fluorescence pattern observed in normal animals. Watkins S. C., Hoffman E. P., Slayter H. S., Kinkel L. M., Immunoelectron microscopic localization of dystrophin in myofibres, *Nature,* Jun. 30, 1988; 333 (6176:863–6). Normal dystrophin expression is localized underneath the plasma membrane of the muscle fiber, so that a cross section of the quadriceps muscle give a fluorescence pattern encircling the cell. In addition dystrophin expression is quantitated by Western blot analysis using the affinity purified anti-60kd antibody.

There will be various modifications, improvements, and applications of the disclosed invention that will be apparent to those of skill in the art, and the present application is intended to cover such embodiments. Although the present invention has been described in the context of certain preferred embodiments, it is intended that the full scope of these be measured by reference to the scope of the following claims.

What is claimed is:

1. A pharmaceutical composition comprising a polynucleotide, viral vector, or polynucleotide derivative thereof in an aqueous dispersion of at least one block copolymer of polyoxyethylene and polyoxypropylene and at least one polycationic homopolymeric, copolymeric, or block copolymeric component having amino-containing monomers, or quaternary salts thereof, which monomers are (a) the same or different cationic amino acid, (b) the same or different units of the formula —NHR°— in which R° is alkylene of 2 to 6 carbon atoms; or (c) the same or different units of the formula —OR$^8$—OP(NH—R$^9$—NH$_2$)(O)— in which R$^9$ is a straight chain aliphatic group of from 1 to 12 carbon atoms and R$^8$ is —(CH$_2$)$_n$—CH(R$^{13}$)— where n is an integer from 0 to 5 and R$^{13}$ is hydrogen cycloalkyl having 3–8 carbon atoms, or alkyl of 1–6 carbon atoms, wherein said block copolymer is present in an amount less than 0.1% (w/v) of said dispersion and insufficient to permit gel formation at ambient temperature.

2. A method of treating a patient comprising parenterally administering a pharmaceutical composition according to claim 1.

3. The method according to claim 2 wherein said pharmaceutical composition is administered intramuscularly.

4. A pharmaceutical composition according to claim 1 wherein the degree of polymerization of each block is between about 5 and about 400.

5. A pharmaceutical composition according to claim 4 wherein the degree of polymerization of each block is between about 5 and about 80.

6. A pharmaceutical composition according to claim 1 wherein the poly(oxyethylene)-poly(oxypropylene) block copolymers contains at least one hydrophilic block component and at least one hydrophobic block component in a weight ratio of hydrophilic:hydrophobic block components is at least 2:1 (w/w), the ethylene oxide content of each hydrophilic block component being more than 50% and the ethylene oxide content of each hydrophobic block component being no more than 50%.

7. A pharmaceutical composition according to claim 6 wherein weight ratio of hydrophilic:hydrophobic blocks is at least 5:1.

8. A pharmaceutical composition according to claim 7 wherein weight ratio of hydrophilic:hydrophobic blocks is at least 8:1.

9. A pharmaceutical composition according to claim 1 wherein the degree of polymerization of each polycationic component is between about 2 and about 300.

10. A pharmaceutical composition according to claim 9 wherein the degree of polymerization of each polycationic component is between about 5 and about 60.

11. A pharmaceutical composition according to claim 1 wherein said polynucleotide, viral vector, or polynucleotide derivative thereof is plasmid DNA.

12. A pharmaceutical composition according to claim 1 in the form of micelles of from about 10 nm to about 100 nm and comprising said homopolymeric, copolymeric, or block copolymeric component.

13. A method of administering a polynucleotide, viral vector, or polynucleotide derivative thereof in which a pharmaceutical composition comprising said polynucleotide, viral vector, or polynucleotide derivative thereof in an aqueous dispersion of one or more block copolymers of polyoxyethylene and polyoxypropylene, said block copolymers being present in an amount less than 0.5% (w/v) of said dispersion and insufficient to permit gel formation at ambient temperature, is administered to said patient.

14. The method according to claim 13 in which the total amount of the one or more block copolymers present in the composition is less than about 0.1% (w/v).

15. The method according to claim 13 in which more than one block copolymer is present in said composition, a first of said block copolymers has an oxyethylene content of 50% or less, and a second of said block copolymers has an oxyethylene content of 50% or more.

16. The method according to claim 15 in which the weight ratio of (i) the block copolymer with oxyethylene content of 50% or less to (ii) the block copolymer with oxyethylene content of 50% or more is 1:2.

17. The method according to claim 15 in which the weight ratio of (i) the block copolymer with oxyethylene content of 50% or less to (ii) the block copolymer with oxyethylene content of 50% or more is 1:5.

18. The method according to claim 13 wherein the dispersion is a suspension, emulsion, microemulsion, micelle, or polymer complex.

19. The method according to claim 18 wherein the dispersion comprises micelles having an average diameter of from about 10 nm to about 100 nm.

20. The method according to claim 18 wherein the dispersion comprises micelles having an average diameter of from about 10 nm to about 25 nm.

21. The method according to claim 13 wherein the composition is administered parenterally.

22. The method according to claim 13 wherein the composition comprises a block copolymer of propylene oxide and ethylene oxide having an average molecular weight of about 12,600.

23. The method according to claim 13 wherein the block copolymer comprises the block copolymer Pluronic L61.

24. The method according to claim 13 wherein the composition comprises a block copolymer of propylene oxide and ethylene oxide having an average molecular weight of about 4,600.

25. The method according to claim 13 wherein the composition comprises a block copolymer of propylene oxide and ethylene oxide having an average molecular weight of about 12,600 and a block copolymer of propylene oxide and ethylene oxide having an average molecular weight of about 2,000.

* * * * *